United States Patent
Altenburger et al.

(10) Patent No.: US 6,680,329 B2
(45) Date of Patent: Jan. 20, 2004

(54) N-(HETEROCYCLYL)BENZENE OR PYRIDINESULPHONAMIDES AS ANTITHROMBOTIC AGENTS AND ANTICOAGULANTS

(75) Inventors: Jean-Michel Altenburger, Saint Remy-les-Chevreuse (FR); Gérard Cremer, Morangis (FR); Gilbert Lassalle, Les Molieres (FR); Mostafa Matrougui, Palaiseau (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 10/221,404

(22) PCT Filed: Mar. 22, 2001

(86) PCT No.: PCT/FR01/00861
§ 371 (c)(1),
(2), (4) Date: Sep. 12, 2002

(87) PCT Pub. No.: WO01/70736
PCT Pub. Date: Sep. 27, 2001

(65) Prior Publication Data
US 2003/0207920 A1 Nov. 6, 2003

(30) Foreign Application Priority Data
Mar. 23, 2000 (FR) .............................. 00 03724

(51) Int. Cl.[7] .................... A61K 31/445; C07D 401/14
(52) U.S. Cl. .................... 514/318; 514/212; 514/231.2; 514/255; 514/256; 514/326; 514/336; 540/484; 544/106; 544/242; 544/333; 544/358; 546/194; 546/212; 546/214; 546/255; 546/280.4; 546/283.4
(58) Field of Search .............. 514/212, 231.2, 514/255, 256, 318, 326, 336; 540/484; 544/242, 333, 358, 106; 546/194, 212, 214, 255, 280.4, 283.4

(56) References Cited

U.S. PATENT DOCUMENTS 5,712,393 A * 1/1998 Altenburger et al. ....... 544/316

FOREIGN PATENT DOCUMENTS

| FR | 2 756 220 A | 5/1998 |
| FR | 2 756 285 A | 5/1998 |
| FR | 2 771 094 A | 5/1999 |

OTHER PUBLICATIONS

Derwent Patent Abstract No. 199828 (1998).
Derwent Patent Abstract No. 199928 (1999).
Derwent Patent Abstract No. 199830 (1998).

* cited by examiner

Primary Examiner—Ceila Chang
(74) Attorney, Agent, or Firm—Paul E. Dupont; Michael D. Alexander

(57) ABSTRACT

Compounds of formula [I]

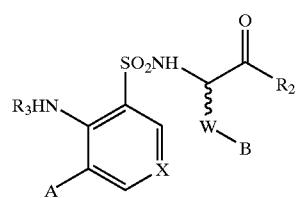

in which:

W may represent a $-(CH_2)_2-$, $-(CH_2)_3-$, $-CH_2-C\equiv C-$ or $-CH_2-CH=CH-$ group, $R_2$ may in particular represent a piperidyl group, an optionally substituted 1,2,3,6-tetrahydropyridyl group, a hexahydro-1H-azepinyl group, an optionally substituted piperazinyl group or a morpholinyl group, $R_3$ may in particular represent a group $-COR_1$, A may in particular represent an optionally substituted phenyl group, a heterocycle or a cyclopentyl group, and B may in particular represent a pyridyl group, an aminopyrazinyl group, an aminopyridazinyl group, a pyrimidinyl group optionally substituted with an amino group, piperidyl group or an aminopyridyl group optionally substituted on the pyridine with a $(C_1-C_4)$ alkyl or $(C_1-C_4)$alkoxy group, the amino group possibly also being substituted with a $(C_1-C_4)$alkyl group, their preparation and their therapeutic application.

29 Claims, No Drawings

N-(HETEROCYCLYL)BENZENE OR PYRIDINESULPHONAMIDES AS ANTITHROMBOTIC AGENTS AND ANTICOAGULANTS

The present invention relates to N-(heterocyclyl)benzene- or -pyridinesulphonamide derivatives, to their preparation and to their therapeutic application.

The compounds of the present invention correspond to formula [I]:

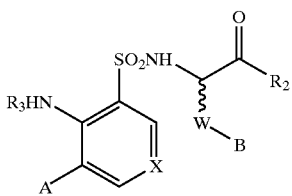

in which:

X represents either a group $=CR_4-$ or a nitrogen atom,

W represents a $-(CH_2)_2-$, $-(CH_2)_3-$, $-CH_2-C\equiv C-$ (triple bond) or $-CH_2-CH=CH-$ (double bond in cis or trans configuration) group, $R_2$ represents
  either a piperidyl group which is optionally substituted:
    with one or two groups chosen from hydroxyl, $(C_1-C_4)$alkyl, hydroxy$(C_1-C_4)$alkyl, $(C_1-C_4)$alkoxy$(C_1-C_4)$alkyl, $(C_1-C_4)$alkoxy, $(C_1-C_4)$alkylthio, monofluoromethyl, difluoromethyl, trifluoromethyl and $(C_3-C_6)$cycloalkyl group,
    with a group $=CYZ$ [Y and Z being chosen, independently of each other, from hydrogen atoms, halogen atoms and $(C_1-C_4)$alkyl groups (optionally substituted with 1 to 3 halogen atoms)],
    with a group:

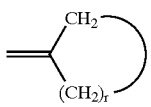

(r=1 to 3) or
  with a spiro[$(C_3-C_6)$cycloalkane] group,
  or a 1,2,3,6-tetrahydropyridyl group optionally substituted with a $(C_1-C_4)$alkyl group (this $(C_1-C_4)$alkyl group being optionally substituted with 1 to 3 halogen atoms) or a $(C_3-C_6)$cycloalkyl group,
  or a hexahydro-1H-azepinyl group optionally substituted in position 4 with a trifluoromethyl or difluoromethylene group,
  or a heptahydroazocin-1-yl group,
  or an octahydro-1H-azonin-1-yl group,
  or a group

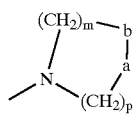

(a-b being a group $-CONR'-$, m=1 to 2, p=1 to 2 and

R' is a hydrogen atom or a $(C_1-C_4)$alkyl group),
or a group

in which
  either $R_{12}$ is a $(C_1-C_4)$alkyl group, a carboxy$(C_1-C_4)$alkyl group or a $(C_1-C_4)$alkoxycarbonyl$(C_1-C_4)$alkyl group and $R_{13}$ is a $(C_1-C_4)$alkoxy or $(C_1-C_4)$alkyl group, or $R_{12}$ is a $(C_1-C_4)$alkyl or $-CH_2CF_3$ group and $R_{13}$ is a
  group

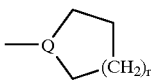

(Q being a carbon or nitrogen atom and r=1 to 3),
  or a piperazinyl group optionally substituted with a $(C_1-C_4)$alkyl group or a $(C_1-C_4)$alkylsulphonyl group,
  or a morpholinyl group,
$R_4$ represents
  either a halogen atom,
  or a hydrogen atom,
$R_3$ represents
  either a $(C_1-C_5)$alkyl group,
  or a group $-COR_1$, in which $R_1$ is either a hydrogen atom or a group $(C_1-C_4)$alkyl, $-(CH_2)_nOCH_3$, $-CH_2O(C_2H_4O)_nCH_3$, $-(CH_2)_nCF_3$ or $-(CH_2)_nOH$ (n=1 to 4),
  or a group $-SO_2R_5$,
  or a group $-CONHR_5$,
  or a group $-SO_2N(R_5)_2$, in which $R_5$ is a $(C_1-C_4)$alkyl group,
A represents
  either a phenyl group optionally substituted with 1 to 3 substituents chosen from
    a halogen atom and
    groups $(C_1-C_4)$alkyl, $(C_1-C_4)$alkoxy, trifluoromethyl, trifluoromethoxy, $-CH_2OR_{10}$, $-CH_2OCOR_{10}$, $-CH_2OCONR_{10}R_{11}$, $-COOR_{10}$, $-CONR_{10}R_{11}$, nitro, $-NR_{10}R_{11}$, $-NHCOR_{10}$ and $-NH(CH_2)_qOR_{10}$, in which $R_{10}$ and $R_{11}$ are, independently of each other, a hydrogen atom or a $(C_1-C_4)$alkyl group and q is between 0 and 6,
  or a heterocycle chosen from pyridyl, thienyl, furyl, pyrimidinyl and thiazolyl groups, the said groups possibly being substituted like the phenyl group above,
  or a $(C_5-C_8)$cycloalkyl group, and B represents
  either a pyridyl group optionally substituted with 1 or 2 substituents chosen from a $(C_1-C_4)$alkyl group, a hydroxyl group and a $(C_1-C_4)$alkoxy group,
  or an aminopyrazinyl group,
  or an aminopyridazinyl group,
  or a pyrimidinyl group optionally substituted with an amino group,
  or a piperidyl group,
  or an aminopyridyl group optionally substituted on the pyridine with a $(C_1-C_4)$alkyl or $(C_1-C_4)$alkoxy group or a halogen atom, the amino group possibly also being substituted with a $(C_1-C_4)$alkyl group, or an aminophenyl group, the amino group possibly being substituted with a $(C_1-C_4)$alkyl group and the phenyl group possibly being substituted with a $(C_1-C_4)$alkyl group or a halogen atom.

In the context of the invention, the terms below have the following meanings:

a $(C_1-C_4)$alkyl group is a linear or branched, saturated hydrocarbon-based chain containing from 1 to 4 carbon atoms, a $(C_x-C_y)$cycloalkyl group is a cyclic hydrocarbon-based chain containing from x to y carbon atoms, a $(C_1-C_4)$alkoxy group is an oxygen radical substituted with a $(C_1-C_4)$alkyl group defined above, a halogen atom is a chlorine, bromine, iodine or fluorine atom.

In the context of the invention, the halogen atoms are preferably chlorine, fluorine and bromine.

Depending on the nature of the group W, the compounds of formula (I) in accordance with the invention may be represented by formulae $(I_1)$, $(I_2)$, $(I_3)$ and $(I_4)$ below:

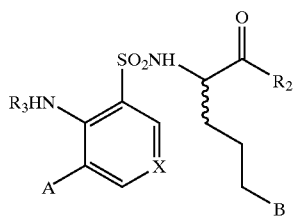

$(I_1)$

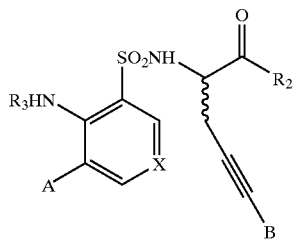

$(I_2)$

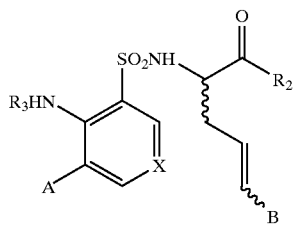

$(I_3)$

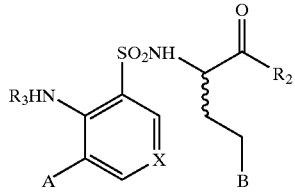

$(I_4)$

The compounds that are preferred according to the invention are the compounds of formula [I] in which:

X, W, $R_4$, A and B are as defined above, $R_2$ represents either a piperidyl group which is optionally substituted:
with one or two groups chosen from hydroxyl, $(C_1-C_4)$alkyl, hydroxy$(C_1-C_4)$alkyl, $(C_1-C_4)$alkoxy$(C_1-C_4)$alkyl, $(C_1-C_4)$alkoxy, $(C_1-C_4)$alkylthio, monofluoromethyl, difluoromethyl, trifluoromethyl and $(C_3-C_6)$ cycloalkyl groups, with a group =CYZ [Y and Z being chosen, independently of each other, from hydrogen atoms, halogen atoms and $(C_1-C_4)$alkyl groups (optionally substituted with 1 to 3 halogen atoms)], or a 1,2,3,6-tetrahydropyridyl group optionally substituted with a $(C_1-C_4)$alkyl group (this $(C_1-C_4)$alkyl group being optionally substituted with 1 to 3 halogen atoms) or a $(C_3-C_6)$cycloalkyl group, or a hexahydro-1H-azepinyl group optionally substituted in position 4 with a trifluoromethyl or difluoromethylene group, or a group

in which $R_{12}$ is a $(C_1-C_4)$alkyl group, a carboxy$(C_1-C_4)$alkyl group or a $(C_1-C_4)$alkoxycarbonyl $(C_1-C_4)$alkyl group and $R_{13}$ is a $(C_1-C_4)$alkoxy or $(C_1-C_4)$alkyl group, or a piperazinyl group optionally substituted with a $(C_1-C_4)$alkyl group or a $(C_1-C_4)$alkylsulphonyl group, or a morpholinyl group, $R_3$ represents either a $(C_1-C_5)$alkyl group, or a group —$COR_1$, in which $R_1$ is either a hydrogen atom or a group $(C_1-C_4)$alkyl, —$(CH_2)_nOCH_3$, —$CH_2O(C_2H_4O)_nCH_3$, —$(CH_2)_nCF_3$ or —$(CH_2)_n$ OH (n=1 to 4).

Among the preferred compounds defined above, the ones that are particularly preferred are the compounds of formula [I] in which:

X, $R_4$ and B are as defined above,

W represents a —$(CH_2)_3$— or —$CH_2$—CH=CH— (double bond in cis or trans configuration) group, $R_2$ represents either a piperidyl group which is optionally substituted:
with one or two groups chosen from hydroxyl, $(C_1-C_4)$alkyl, hydroxy$(C_1-C_4)$alkyl, $(C_1-C_4)$alkoxy$(C_1-C_4)$alkyl, $(C_1-C_4)$alkoxy, $(C_1-C_4)$alkylthio, monofluoromethyl, difluoromethyl and trifluoromethyl groups, with a group =CYZ [Y and Z being chosen, independently of each other, from hydrogen atoms, halogen atoms and $(C_1-C_4)$alkyl groups (optionally substituted with 1 to 3 halogen atoms)], or a 1,2,3,6-tetrahydropyridyl group optionally substituted with a $(C_1-C_4)$alkyl group (this $(C_1-C_4)$alkyl group being optionally substituted with 1 to 3 halogen atoms), or a hexahydro-1H-azepinyl group, or a piperazinyl group optionally substituted with a $(C_1-C_4)$alkylsulphonyl group, or a morpholinyl group, $R_3$ represents a group —$COR_1$, in which $R_1$ is a group $(C_1-C_4)$alkyl, —$(CH_2)_nOCH_3$ or —$(CH_2)_nCF_3$ (n=1 to 4), A represents
- either a phenyl group optionally substituted with 1 to 3 substituents chosen from
  - a halogen atom and
  - ($C_1$–$C_4$)alkyl and ($C_1$–$C_4$)alkoxy groups,
- or a heterocycle chosen from pyridyl and thienyl groups,
- or a ($C_5$–$C_8$)cycloalkyl group.

The preferred configuration of the central amino acid portion of the compounds in accordance with the present invention:

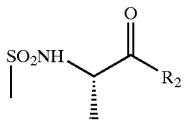

is [S]

The compounds of formula [I] in accordance with the invention may exist in the form of racemates or pure enantiomers or mixtures of enantiomers. They may also exist in the form of acids or free bases or addition salts with pharmaceutically acceptable acids, for example in the form of hydrochloride or methanesulphonate.

Mention may be made in particular of the following compounds, in the form of racemates or pure enantiomers or mixtures of enantiomers, or alternatively in the form of acids or free bases, of hydrochloride or of any other pharmaceutically acceptable salt, which form a part of the invention:

N-[2-[[[(1S)-4-(5-amino-3-methylpyrid-2-yl)-1-[[4-(difluoromethylene)piperid-1-yl]carbonyl]butyl]amino]sulphonyl]-6-thien-2-ylphenyl]propanamide, N-[2-[[[(1S)-4-(6-amino-4-ethylpyrid-3-yl)-1-[[4-(difluoromethylene)piperid-1-yl]carbonyl]butyl]amino]sulphonyl]-6-cyclopentylphenyl]acetamide, N-[3-[[[(1S)-4-(5-aminopyrid-2-yl)-1-[[4-(difluoromethylene)piperid-1-yl]carbonyl]butyl]amino]sulphonyl]-3'-fluoro[1,1'-diphenyl]-2-yl]propanamide, N-[3-[[[(1S)-4-(5-aminopyrid-2-yl)-1-[[4-(difluoromethylene)piperid-1-yl]carbonyl]butyl]amino]sulphonyl]-3'-fluoro[1,1'-diphenyl]-2-yl]acetamide, N-[2-[[[(1S)-4-(5-aminopyrid-2-yl)-1-[(4-ethylpiperid-1-yl)carbonyl]butyl]amino]sulphonyl]-6-thien-2-ylphenyl]propanamide, N-[2-[[[(1S)-4-(6-aminopyrid-3-yl)-1-piperid-1-ylcarbonyl)butyl]amino]sulphonyl]-6-cyclopentylphenyl]propanamide, N-[2-[[[(1S)-4-(5-aminopyrid-2-yl)-1-[[4-(difluoromethylene)piperid-1-yl]carbonyl]butyl]amino]sulphonyl]-6-cyclopentylphenyl]propanamide, N-[3-[[[(1S)-4-(5-aminopyrid-2-yl)-1-[[4-(difluoromethylene)piperid-1-yl]carbonyl]butyl]amino]sulphonyl][1,1'-diphenyl]-2-yl]acetamide, N-[2-[[[(1S)-4-(6-aminopyrid-3-yl)-1-[[4-(difluoromethylene)piperid-1-yl]carbonyl]butyl]amino]sulphonyl]-6-thien-2-yl-phenyl]acetamide, N-[2-[[[(1S)-4-(6-amino-4-methylpyrid-3-yl)-1-[[4-(difluoromethylene)piperid-1-yl]carbonyl]butyl]amino]sulphonyl]-6-thien-2-ylphenyl]propanamide, N-[2-[[[(1S)-4-(6-aminopyrid-3-yl)-1-[[4-(difluoromethylene)piperid-1-yl]carbonyl]butyl]amino]sulphonyl]-6-cyclopentylphenyl]acetamide, N-[2-[[[(1S)-4-(aminopyrid-3-yl)-1-[[4-(trifluoromethyl)-1,2,3,6-tetrahydropyrid-1-yl]carbonyl]butyl]amino]sulphonyl]-6-thien-2-yl-phenyl]propanamide, N-[2-[[[(1S)-4-(6-aminopyrid-3-yl)-1-[[4-(difluoromethylene)piperid-1-yl]carbonyl]butyl]amino]sulphonyl]-6-cyclopentylphenyl]propanamide, N-[3-[[[(1S)-4-(5-aminopyrid-2-yl)-1-[[4-(difluoromethylene)piperid-1-yl]carbonyl]butyl]amino]sulphonyl][1,1'-diphenyl]-2-yl]propanamide, N-[2-[[[(1S)-4-(6-amino-4-methylpyrid-3-yl)-1-[[4-difluoromethylene)piperid-1-yl]carbonyl]butyl]amino]sulphonyl]-6-cyclopentylphenyl]propanamide, N-[3-[[[(1S)-4-(6-aminopyrid-3-yl)-1-[[4-(difluoromethylene)piperid-1-yl]carbonyl]butyl]amino]sulphonyl]-3'-fluoro[1,1'-diphenyl]-2-yl]propanamide, N-[2-[[[(1S)-4-(5-aminopyrid-2-yl)-1-[(4-methylpiperid-1-yl)carbonyl]butyl]amino]sulphonyl]-6-thien-2-ylphenyl]acetamide, N-[2-[[[(1S)-4-(6-aminopyrid-3-yl)-1-[(4-ethylpiperid-1-yl)carbonyl]butyl]amino]sulphonyl]-6-thien-2-ylphenyl]propanamide, N-[2-[[[(1S)-4-(6-aminopyrid-3-yl)-1-[(4-methylpiperid-1-yl)carbonyl]butyl]amino]sulphonyl]-6-cyclopentylphenyl]acetamide, N-[3-[[[(1S)-4-(5-aminopyrid-2-yl)-1-[(4-methylpiperid-1-yl)carbonyl]butyl]amino]sulphonyl]-3'-methyl[1,1'-diphenyl]-2-yl]acetamide, N-[3-[[[(1S)-4-(6-amino-4-methoxypyrid-3-yl-1-[[4-(difluoromethylene)piperid-1-yl]carbonyl]butyl]amino]sulphonyl][1,1'-diphenyl]-2-yl]propanamide, N-[3-[[[(1S)-4-(5-aminopyrid-2-yl)-1-[(4-methylpiperid-1-yl)carbonyl]butyl]amino]sulphonyl]-3'-methyl[1,1'-diphenyl]-2-yl]propanamide, N-[3-[[[(1S)-4-(5-aminopyrid-2-yl)-1-[(4-methylpiperid-1-yl)carbonyl]butyl]amino]sulphonyl]-3'-fluoro[1,1'-diphenyl]-2-yl]acetamide, N-[3-[[[(1S)-4-(5-aminopyrid-2-yl)-1-[(4-methylpiperid-1-yl)carbonyl]butyl]amino]sulphonyl]-3'-methoxy[1,1'-diphenyl]-2-yl]propanamide, N-[(1S)-4-(5-amino-2-pyridyl)-1-[[4-(difluoromethylene)-1-piperidyl]carbonyl]butyl]-2-(formylamino)-3'-methyl[1,1'-diphenyl]-3-sulphonamide, N-[3-[[[(1S,3Z)-4-(5-amino-2-pyridyl)-1-[[4-(difluoromethylene)-1-piperidyl]carbonyl]-3-butenyl]amino]sulphonyl][1,1'-diphenyl]-2-yl]acetamide, N-[3-[[[(1S,3Z)-4-(5-amino-2-pyridyl)-1-[(4-methyl-1-piperidyl)carbonyl]-3-butenyl]amino]sulphonyl][1,1'-diphenyl]-2-yl]acetamide.

A subject of the invention is also a medicinal product, characterized in that it contains at least one compound of formula (I) as defined above.

A subject of the invention is also a pharmaceutical composition, characterized in that it contains at least one compound of formula (I) as defined above, as well as at least one pharmaceutically acceptable excipient.

With reference to Scheme 1, in order to obtain the compounds of formula [I] in accordance with the present invention in which X represents a group =$CR_4$—, a compound of formula [V] in which $P_1$ is a protecting group for an amine function, in particular a tert-butoxycarbonyl (Boc) group, B and W are as defined above and P is either a protecting group such as phenylmethoxycarbonyl or a hydrogen atom, is reacted, in a step (i), with a compound of formula [VI], in which $R_2$ is as defined above. A compound of formula [IV] is thus obtained, which is treated with hydrogen chloride in a step (ii) to give a compound of formula [III].

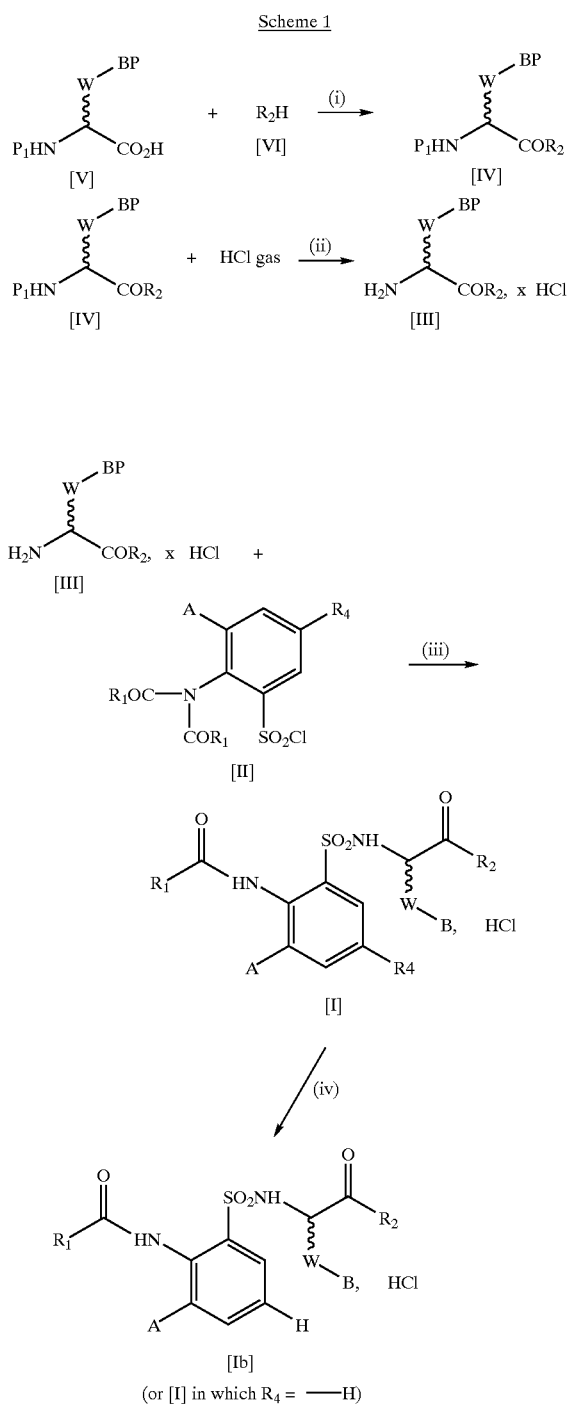

In a step (iii), the compound of formula [III] is coupled, in the presence of triethylamine, with a compound of formula [II] in which $R_1$, $R_4$ and A are as defined above, to give, after treatment with ammonia, a compound of formula [I]. The modification of the group —NHCOR$_1$ into a group —NHR$_3$ as defined above in relation to formula [I] is carried out according to the techniques of organic chemistry that are known to those skilled in the art.

When it is desired to obtain a compound of formula [I] in which $R_4$ is a hydrogen atom, a hydrogenolysis of compound [I] is then carried out in a step (iv) to give a compound of formula [Ib].

According to one preferred embodiment of the process for preparing the compounds of formula (I) of the present invention, the step (i) mentioned above may be carried out in the presence of N,N-diisopropylethylamine (DIEA) in dichloromethane or in dimethylformamide by adding, under nitrogen, O-(1-benzotriazolyl)-N,N,N',N'-tetramethyluronium hexafluorophosphate (HBTU), step (ii) may be carried out in dichloromethane in the presence of hydrogen chloride gas, step (iii) may be carried out first in dichloromethane and triethylamine (TEA) and then by taking up the product obtained in tetrahydrofuran (THF) and then passing a stream of ammonia through, followed by treatment with 0.1 N hydrogen chloride in isopropanol, or with hydrogen bromide in acetic acid, step (iv) may be carried out by taking up the compound of formula [I] in a 0.1 N solution of hydrogen chloride and in isopropanol.

According to one variant of the process in accordance with the present invention, the compounds of formula [I], in which X represents a group =CR$_4$—, are also prepared in accordance with Scheme 2. With reference to Scheme 2, these compounds may be prepared by reacting, in a step (i), the compound of formula [III] as obtained in step (ii) of the process of the invention described above (Scheme 1) [with P=a hydrogen atom] with a compound of formula [IIa], in which $R_4$ is a halogen atom and $R_1$ is as defined above. A compound of formula [Ia] is thus obtained, which is coupled with a compound of formula [VII] in which A is as defined above and $R_5$ is a (C$_1$–C$_4$)alkyl group, to give a compound of formula [I]. When it is desired to obtain a compound of formula [I] in which $R_4$ is a hydrogen atom, a hydrogenolysis of compound [I] is then carried out in a step (iii) to give a compound of formula [Ib].

According to one preferred embodiment of this variant of the process for preparing the compounds of formula [I] of the present invention, in which X represents a group =CR$_4$—, step (i) mentioned above may be carried out first in dichloromethane, in the presence of triethylamine, and then by next taking up the product obtained in a stream of ammonia, Scheme 2

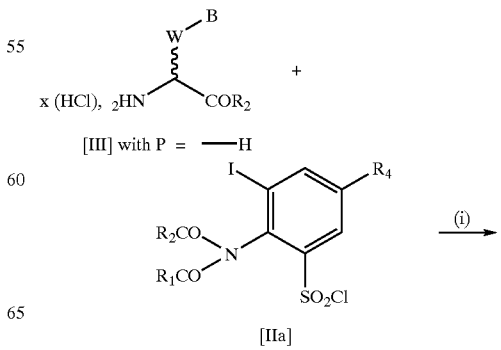

-continued

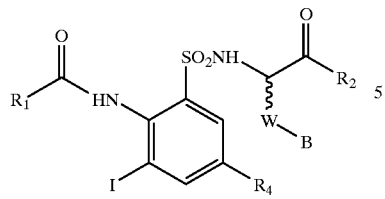

[Ia]

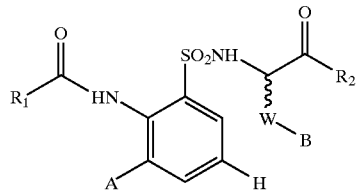

[Ib]

(or [I] in which R₄ = ——H)

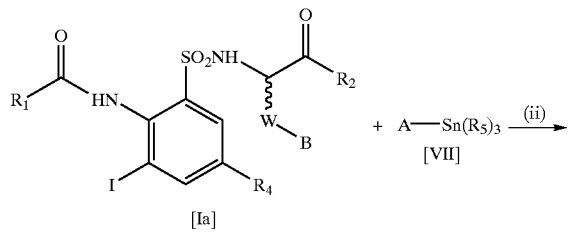

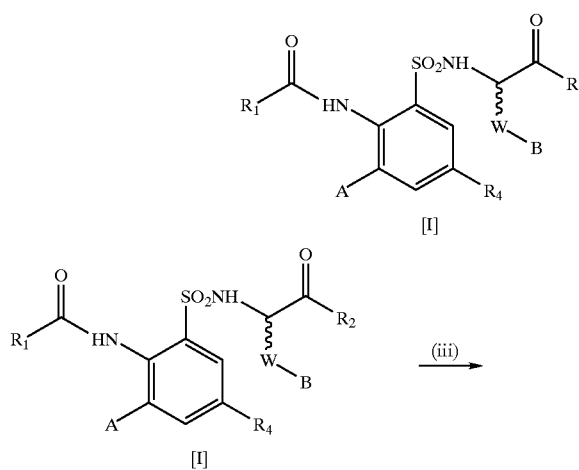

step (ii) may be carried out in a mixture of copper iodide and triphenylarsine (Ph₃As) in anhydrous dimethylformamide (DMF) and by adding bisdibenzylideneacetonepalladium (0) [Pd(dba)₂], step (iii) may be carried out in the presence of active palladium-on-charcoal (Pd-c), and ammonium formate in methanol, step (iv) may be carried out by taking up the compound of formula [I] in a 0.1 N solution of hydrogen chloride and in isopropanol.

The compounds of formula [V] of the present invention, as represented in Scheme 1, are prepared according to Schemes 3 and 4.

Schemes 3 and 4 illustrate the preparation of various types of compounds of formula [V], namely:

the compound of formula [Ve], which is useful as an intermediate in the preparation of compounds of formula (I) in which W=CH₂—CH=CH— (the double bond being in cis configuration), the compound of formula [Vg], which is useful as an intermediate in the preparation of compounds of formula (I) in which W=—CH₂—CH=CH— (the double bond being in trans configuration), the compound of formula [Vh], which is useful as an intermediate in the preparation of compounds of formula (I) in which W=—(CH₂)₃—, the compound of formula [Vc], which is useful as an intermediate in the preparation of compounds of formula (I) in which W=CH₂—C≡C—, the compound of formula [Vi], which is useful as an intermediate in the preparation of compounds of formula (I) in which W=—(CH₂)₂—.

Scheme 3

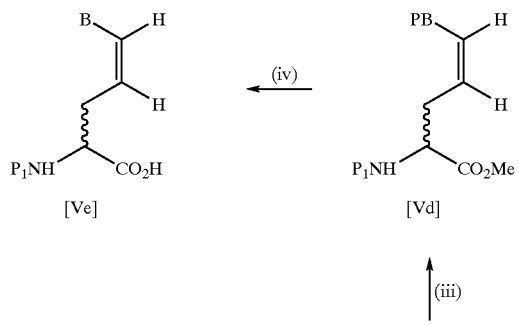

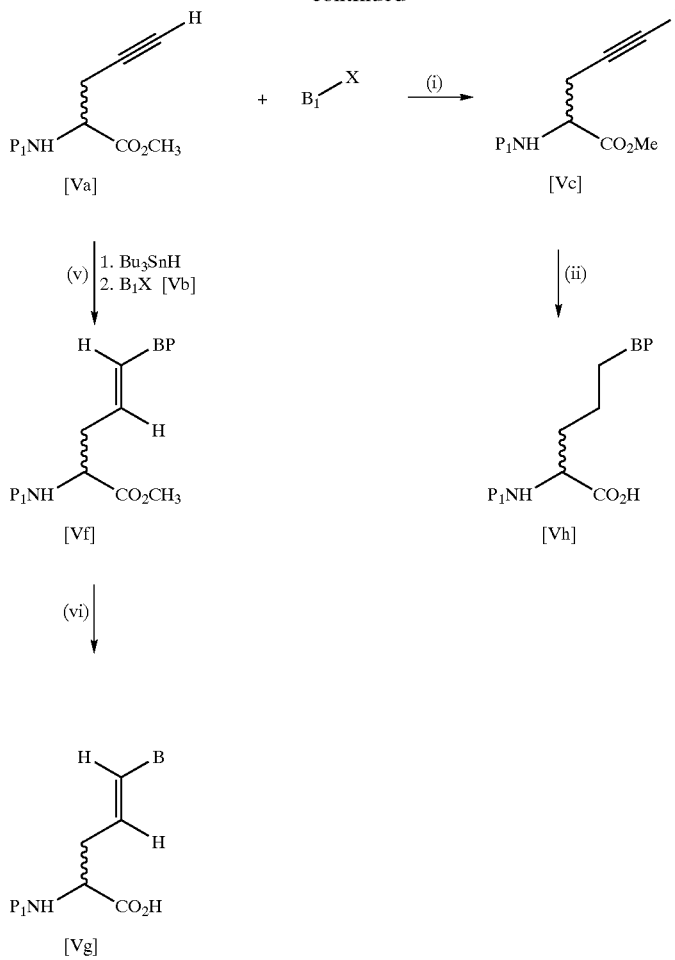

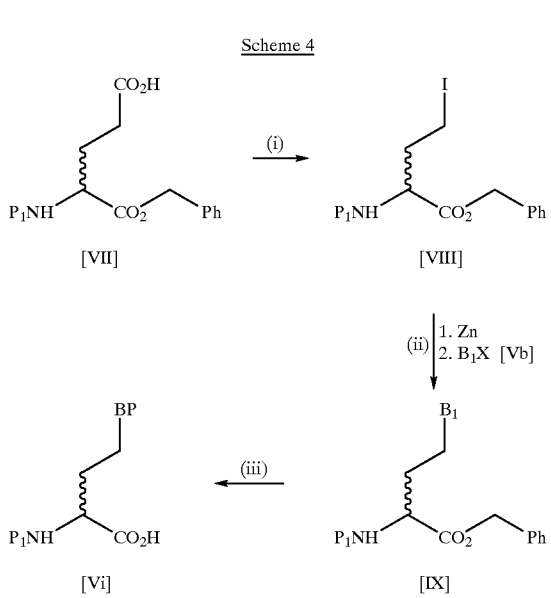

To prepare the compound of formula [Vc], the following steps are carried out, for example (Scheme 3):

in a step (i), and by analogy with the synthesis disclosed in patent application WO 97/40052, a compound of formula [Va] in which $P_1$ is as defined above, is reactedwith a compound of formula [Vb] in which $B_1$ is an aromatic base bearing either a protected or unprotected primary or secondary amine function, or a precursor of an amine function such as a nitro group, and X represents a halogen atom, to give a compound of formula [Vc].

To convert the compound of formula [Vc] into a compound of formula [V] which may be used directly in the process represented in Scheme 1, a saponification of the ester group is carried out, and, when $B_1$ bears a precursor of an amine function, this precursor is converted into an amine group optionally protected with a group P, by means of the techniques of organic chemistry that are known to those skilled in the art.

To prepare the compound of formula [Vh], the following steps are carried out, for example (Scheme 3):

in step (ii), the compound of formula [Vc] is subjected either to a total hydrogenation, both of the triple bond and of the nitrogen heterocycle, optionally followed by a conventional orthogonal protection of the non-aromatic secondary amine which may be generated, with a group P such as phenylmethoxycarbonyl, or to a selective hydrogenation of the triple bond, followed by a saponification, to give the compound of formula [Vh].

To prepare the compound of formula [Ve], the following steps are carried out, for example (Scheme 3):

in a step (iii), compound [Vc] is subjected to a controlled hydrogenation of the triple bond, optionally followed by a conventional orthogonal protection of the secondary amine of the amine borne by the group B, with a group P such as tert-butoxycarbonyl (Boc). In a step (iv), a saponification of the ester group of compound [Vd] is carried out to give compound [Ve].

To prepare the compound of formula [Vg], the following steps are carried out, for example (Scheme 3):

in a step (v), compound [Va] is subjected first to a hydrostannylation of the triple bond, followed by a catalysed coupling via a palladium complex with a compound [Vb] in which $B_1$ is an aromatic base bearing either a protected or unprotected primary or secondary amine function, or a precursor of an amine function such as a nitro group, and X represents a halogen atom, to give the compounds of formula [Vf], in a step (vi), the ester group of the compound [Vf] is hydrolysed to give the compound of formula [Vg].

According to one preferred embodiment of the process for preparing the compounds of formula [V] of the present invention, as illustrated in Scheme 3:

step (i) mentioned above may be carried out in dimethylformamide, in the presence of a palladium-based catalyst such as the dichlorobis(triphenylphosphine)palladium/cuprous iodide complex, in basic medium, for example with potassium bicarbonate and in anhydrous dimethylformamide, step (ii) mentioned above may be carried out with molecular hydrogen or ammonium formate, in methanol, in the presence of a palladium-based catalyst such as active palladium-on-charcoal, and by carrying out the saponification with lithium hydroxide in a methanol/water mixture, step (iii) mentioned above may be carried out in the presence of palladium on barium sulphate in ethyl acetate. When B1 bears a nitro function, it is desirable to reduce it beforehand, preferably with iron in an ethanol/acetic acid mixture, step (iv) leading to the compounds [Ve] may be carried out with lithium hydroxide in a methanol/water mixture, step (v) may be carried out with a compound [Va] bearing a protecting group P1 such as trityl in order to improve the regioselectivity of the hydrostannylation reaction. This is carried out with tributyltin hydride in tetrahydrofuran in the presence of tetrakis(triphenylphosphine)palladium (0). The coupling with the electrophilic reagent [Vb] is carried out in anhydrous dioxane in the presence of tetrakis(triphenylphosphine)palladium (0), when the group $P_1$ of the compound of formula [Vf] is a trityl, step (vi) consists in converting the group $P_1$ of trityl type into a tert-butyloxycarbonyl group in the presence of aqueous sodium hydroxide using bis(di-tert-butyl) carbonate. In this operation, the methyl ester is hydrolysed to carboxylic acid, thus giving the compound of formula [Vg].

With reference to Scheme 4, the intermediate compounds of formula [Vi] may be prepared, thus making it possible to prepare the compounds of formula [I] in which W is a —$(CH_2)_2$— group, in the following way:

in a step (i), a compound of formula [VII] derived from glutamic acid, in which $P_1$ is as defined above and Ph represents a phenyl group, is subjected to a Hunsdiecker reaction to give the compound of formula [VIII], in a step (ii), the compound of formula [VIII] is converted into the corresponding organozinc derivative, which is coupled in situ, via catalysis with palladium, to a compound of formula [Vb] in which $B_1$ is as defined above and X represents a halogen atom, to give the compounds of formula [IX], in a step (iii), the compound of formula [IX] is hydrogenated on a palladium catalyst to give the compound of formula [Vi] bearing a free carboxylic acid function.

According to one preferred embodiment of this process for preparing the compounds of formula [Vi] of the present invention, step (i) mentioned above may be carried out in carbon tetrachloride under argon, in the presence of di(acetyloxy)iodobenzene and molecular iodine. This step is thus carried out under UV irradiation, step (ii) mentioned above may be carried out in dimethylformamide under argon in the presence of zinc powder activated by adding trimethylsilyl chloride and 1,2-dibromoethane. The organozinc derivative thus prepared is then treated with the electrophile $B_1X$, for example in the presence of tris(dibenzylideneacetone)dipalladium and tri-ortho-tolylphosphine at room temperature, step (iii) mentioned above may be carried out in a methanol/water mixture in the presence of active 10% palladium-on-charcoal catalyst and at 50 psi of hydrogen.

With reference to Scheme 5, in order to obtain the compounds of formula [XV], which are useful as intermediates for preparing the compounds of formula [I] in accordance with the invention in which X=N, the following steps are carried out:

in a step (i), a 4-aminopyridine compound of formula [X] in which the amine function is protected with a protecting group P1 as defined above, is converted into a derivative of formula [XI] bearing two bromine atoms positioned beforehand to introduce the desired groups, in a step (ii), the compound of formula [XI] is coupled with a boronic acid derivative of formula $AB(OH)_2$ in which A is a phenyl nucleus or a heterocycle which is optionally substituted, in the presence of a palladium catalyst, to give a compound of formula [XII], Scheme 5

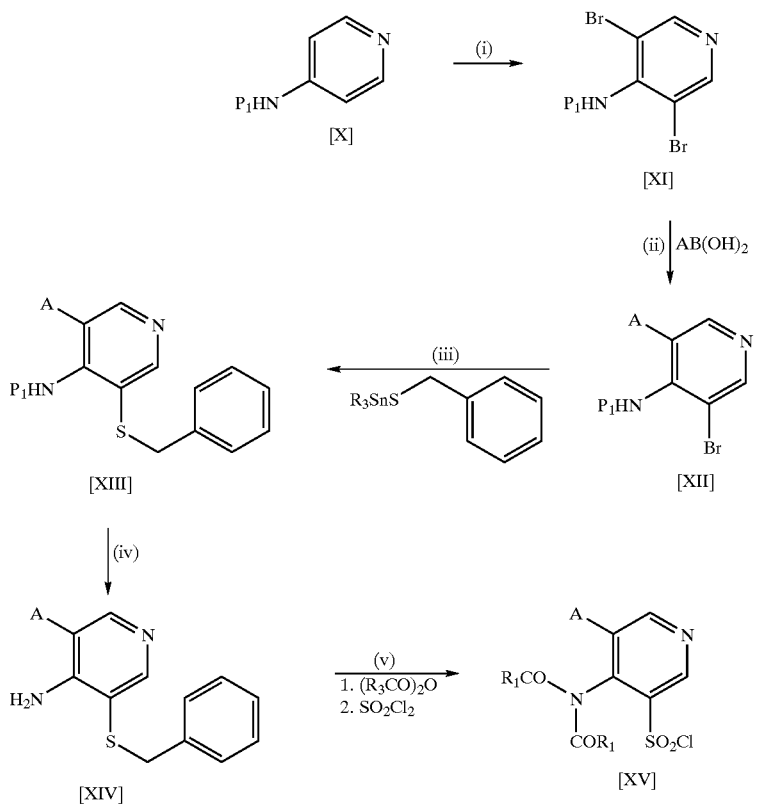

in a step (iii), the sulphur atom which is the precursor of the sulphonyl chloride group is introduced via a palladium-catalysed coupling reaction between the compound of formula [XII] and an organotin derivative prepared beforehand from benzenemethanethiol, in a step (iv), the protecting group $P_1$ is removed by acidic treatment under conventional conditions to give the compound of formula [XIV], in a step (v), the compound of formula [XIV] is converted into a mixed imide by treatment with an anhydride, and the benzylthiol group is then directly oxidized to the chlorosulphonyl derivative of formula [XV] with sulphuryl chloride in the presence of acetic acid and water.

According to one preferred embodiment of this process for preparing the compounds of formula [XV]:

step (i) mentioned above may be carried out in acetonitrile with N-bromosuccinimide, step (ii) mentioned above may be carried out in a dioxane/water mixture in the presence of sodium carbonate and tetrakis(triphenylphosphine)palladium (0), step (iii) mentioned above may be carried out in anhydrous dioxane in the presence of tetrakis(triphenylphosphine)palladium (0) with tributyl [(phenylmethyl)thio]stannane prepared beforehand, step (iv) mentioned above may be carried out conventionally in methanol in the presence of a stream of hydrogen chloride, step (v) mentioned above may be carried out by heating in a pure anhydride such as propionic anhydride. After evaporating off the excess reagent, a treatment in a mixture of acetic acid and water with sulphuryl chloride gives the expected chlorosulphonyl compound of formula [XV] directly.

The compound of formula [XV] thus obtained may then be used to prepare the compounds of formula [I] in accordance with the invention in which X=N, by following the protocol described in step (iii) of Scheme 1, i.e. by coupling the compound of formula [XV] with a compound of formula [III] as defined above.

The starting compounds, such as the compound of formula [Vb] are commercially available or are described in the literature, or alternatively may be prepared according to methods which are described therein or which are known to those skilled in the art.

The examples which follow illustrate the preparation of certain compounds in accordance with the invention. The microanalyses and the IR and NMR spectra confirm the structure of the compounds obtained.

The numbers for the compounds illustrated refer to those in the tables given later, which illustrate the chemical structures and physical properties of a number of compounds according to the invention. The ratio (x:y) represents the (acid:base) ratio.

EXAMPLE 1 (COMPOUND 3)

(S)-N-[2-[[[4-(6-aminopyrid-3-yl)-1-[(4-ethylpiperid-3-yl)carbonyl]butyl]amino]sulphonyl]-6-thien-2-yl-phenyl]propanamide hydrochloride 1.1. N-(5-bromopyrid-2-yl)-2,2,2-trifluoroacetamide 68.0 ml (0.477 mol) of a solution of trifluoroacetic anhydride in 250 ml of dichloromethane are added dropwise at 0° C., under nitrogen, to a solution of 75.0 g (0.433 mol) of 5-bromo-2-pyridinamine and 41.25 ml (0.519 mol) of pyridine in 250 ml of dichloromethane. The mixture is allowed to warm gently to room temperature and stirring is continued for 18 hours. The reaction mixture is diluted with 300 ml of dichloromethane and is then washed with water (2×400 ml) and then in saturated sodium chloride solution (2×200 ml), after which it is dried over sodium sulphate and concentrated under reduced pressure. The residue obtained is purified by chromatography on a column of gel, eluting under pressure with a dichloromethane/pentane (1:1) mixture. 100 g of N-(5-bromopyrid-2-yl)-2,2,2-trifluoroacetamide are obtained in the form of a white solid.

Yield (%)=86; m.p. (°C.)=73.

1.2. Methyl (S)-2-[[(1,1-dimethylethoxy)carbonyl]amino]-5-[6-[(trifluoroacetyl)amino]pyrid-3-yl]pent-4-ynoate 1.7 g (2.4 mmol) of dichlorobis(triphenylphosphine) palladium are added at room temperature, under argon, to a mixture of 13.0 g (48.3 mmol) of N-(5-bromo-2-pyridyl)-2,2,2-trifluoroacetamide, 16.0 g (70.5 mmol) of methyl (S)-2-[[(1,1-dimethylethoxy)carbonyl]amino]pent-4-ynoate, 0.46 g (2.4 mmol) of copper iodide and 13.35 g (96.6 mmol) of potassium carbonate in 25 ml of anhydrous dimethylformamide (DMF). The mixture is heated for 5 hours at 65° C. The mixture is taken up in ether (800 ml) and then washed with water (2×600 ml) and then with saturated sodium chloride solution (300 ml) and is dried over sodium sulphate. The product obtained is filtered and then concentrated under reduced pressure. The residue obtained is purified by chromatography on a column of silica gel, eluting under pressure with an ethyl acetate/cyclohexane gradient of from 0 to 20% ethyl acetate. 10 g of methyl (S)-2-[[(1,1-dimethylethoxy)carbonyl]amino-5-[6-(trifluoroacetyl)amino]pyrid-3-yl]pent-4-ynoate are thus obtained in the form of an oil.

Yield (%)=52

1.3. (S)-6-Amino-α-[[(1,1-dimethylethoxy)carbonyl]amino]pyridine-3-pentanoic acid A mixture of 8.04 g of methyl (S)-2-[[(1,1-dimethylethoxy)carbonyl]amino]-5-[6-(trifluoroacetyl)amino]pyrid-3-yl)pent-4-ynoate (20 mmol) and active 10% palladium-on-charcoal (0.8 g) in methanol (80 ml) and acetic acid (1.32 ml; 22 mmol) is stirred for 7 hours under 50 psi of hydrogen at room temperature. The mixture is filtered and is then concentrated under reduced pressure. The residue obtained is taken up in ethyl acetate (400 ml) and then washed with saturated sodium hydrogen carbonate solution (200 ml) and saturated sodium chloride solution (200 ml), filtered and dried over sodium sulphate and is then concentrated under reduced pressure. Lithium hydroxide monohydrate (1.1 g, 26 mmol) is added, at 0° C., to a solution of the residue thus obtained in methanol (50 ml) and water (15 ml). The mixture is allowed to warm to room temperature and stirring is continued for 18 hours. The reaction mixture is cooled to 0° C., neutralized with 1N hydrochloric acid solution and then concentrated under reduced pressure. 7 g of (S)-6-amino-α-[[(1,1-dimethylethoxy)carbonyl]amino]pyridine-3-pentanoic acid (lithium chloride) are obtained in the form of a viscous oil, which is used without further purification in the following step.

Yield (%)=88

1.4. 1,1-Dimethylethyl (S)-[4-(6-aminopyrid-3-yl)-1-([4-ethylpiperid-3-yl)carbonyl]butyl]carbamate 2.1 g (5.5 mmol) of O-(benzotriazol-1l-yl)-N,N,N',N'-tetramethyluronium hexafluorophosphate (HBTU) are added portionwise with stirring, at 0° C. under nitrogen, to a mixture of 2.0 g of (S)-6-amino-α-[[(1,1-dimethylethoxy)carbonyl]amino]pyridine-3-pentanoic acid (5.5 mmol), 1.14 g (7.5 mmol) of 4-ethylpiperidine hydrochloride, N,N-diisopropylethylamine (DIEA) (25 ml; 14 mmol) in dichloromethane (30 ml) and 3 ml of anhydrous dimethylformamide (DMF). The mixture is allowed to warm to room temperature and stirring is continued for 18 hours. The reaction mixture is taken up in 250 ml of ethyl acetate and is washed with 50 ml of 0.1 N hydrochloric acid solution and with 50 ml of saturated sodium hydrogen carbonate solution and with 50 ml of saturated sodium chloride solution. The product obtained is then dried over sodium sulphate and then filtered and concentrated under reduced pressure. The residue obtained is purified by chromatography on a column of silica gel, eluting under pressure with ethyl acetate. 1.48 g of 1,1-dimethylethyl (S)-[4-(6-aminopyrid-3-yl)-1-([4-ethylpiperid-3-yl)carbonyl]butyl]carbamate are obtained in the form of a viscous oil.

Yield (%)=74

1.5. (S)-1-[2-Amino-5-(6-aminopyrid-3-yl)-1-oxopentyl]-4-ethylpiperidine hydrochloride (2:1)

A solution of 1.48 g (3.6 mmol) of 1,1-dimethylethyl (S)-[4-(6-aminopyrid-3-yl)-1-[(4-ethylpiperid-3-yl)carbonyl]butyl]carbamate in 40 ml of dichloromethane is treated for 1 min at 0° C. with a stream of hydrogen chloride. After one hour at 0° C., the reaction mixture is allowed to warm to room temperature and is then concentrated under reduced pressure. 1.4 g of (S)-1-[2-amino-5-(6-aminopyrid-3-yl)-1-oxopentyl]-4-ethylpiperidine hydrochloride (2:1) are obtained in the form of a white solid, which is used without further purification in the following step.

Yield (%)=100; m.p. (°C.)=65.

1.6. (S)-N-[2-[[[4-(6-aminopyrid-3-yl)]-1-(4-ethylpiperid-3-yl)carbonyl]butyl]amino]sulphonyl]-6-thien-2-ylphenyl]propanamide hydrochloride 1.84 ml (13.2 mmol) of triethylamine (TEA) are added, at 0° C., to a solution of 1.5 g (4 mmol) of (S)-1-[2-amino-5-(6-aminopyrid-3-yl)-1-oxopentyl]-4-ethylpiperidine hydrochloride (2:1) in 20 ml of dichloromethane, followed by portionwise addition of 1.54 g (4 mmol) of 2-[bis(1-oxopropyl)amino]-3-thien-2-ylbenzenesulphonyl chloride. After 4 h at 0° C., 200 ml of ethyl acetate are added and the mixture is then washed with 100 ml of saturated sodium hydrogen carbonate solution and 100 ml of saturated sodium chloride solution. The product obtained is dried over sodium sulphate and concentrated under reduced pressure. The residue thus obtained is taken up in 100 ml of tetrahydrofuran (THF) and is then cooled to 0° C. and treated for 5 minutes with a stream of ammonia. The reaction mixture is allowed to warm to room temperature and, after 4 hours, is then concentrated under reduced pressure. The residue obtained is taken up in 50 ml of a 0.1N solution of hydrogen chloride in isopropanol (5 mmol) and is then concentrated under reduced pressure and purified by chromatography on an RP 18 column, eluting with an acetonitrile/water gradient of from 5/95 to 30/70. 2 g of (S)-N-[2-[[[4-(6-aminopyrid-3-yl)]-1-(4-ethylpiperid-3-yl)carbonyl]butyl]amino]sulphonyl]-6-thien-2-ylphenyl]propanamide hydrochloride are obtained.

Yield (%)=79; m.p. (°C.)=144–148;
$[\alpha]_D^{20}$ (°)=+120 (c=0.2; methanol)

EXAMPLE 2 (COMPOUND 5)

(S)-N-[2-[[[4-(6-aminopyrid-3-yl)-1-[(4-ethylpiperid-3-yl)carbonyl]butyl]amino]sulphonyl]-4-pyrid-2-yl-phenyl]propanamide hydrochloride (2:1)

2.1. (S)-N-[2-[[[4-(6-aminopyrid-3-yl)-1-[(4-ethylpiperid-3-yl)carbonyl]butyl]amino]sulphonyl]-4-bromo-6-iodophenyl]propanamide The same procedure as in Example 1.6 is used, except for the treatment with a 0.1N solution of hydrogen chloride in isopropanol and the purification by chromatography on an RP18 column. Thus, starting with 1.4 g (3.6 mmol) of (S)-1-[2-amino-5-(6-aminopyrid-3-yl)-1-oxopentyl]-4-ethylpiperidine hydrochloride (2:1) and 1.88 g (3.6 mmol) of 2-[bis(1-oxopropyl)amino]-5-bromo-3-iodobenzenesulphonyl chloride, 1.9 g of (S)-N-[2-[[[4-(6-aminopyrid-3-yl)-1-[(4-ethylpiperid-3-yl)carbonyl]butyl]amino]sulphonyl]-4-bromo-6-iodophenyl]propanamide are obtained in the form of a white powder.

Yield (%)=81; m.p. (°C.)=193.

2.2. (S)-N-[2-[[[4-(6-Aminopyrid-3-yl)-1-[(4-ethylpiperid-3-yl)carbonyl]butyl]amino]sulphonyl]-4-bromo-6-pyrid-2-ylphenyl]propanamide 0.08 g (0.14 mmol) of bis(dibenzylideneacetone)palladium (0) is added, at room temperature, to a mixture of 1.8 g (2.76 mmol) of (S)-N-[2-[[[4-(6-aminopyrid-3-yl)]-1-[(4-ethylpiperid-3-yl)carbonyl]butyl]amino]sulphonyl]-4-bromo-6-iodophenyl]propanamide, 1.22 g (3.32 mmol) of 2-(tributylstannyl)pyridine, 0.052 g (0.28 mmol) of copper iodide and 0.17 g (0.56 mmol) of triphenylarsine in 6 ml of anhydrous dimethylformamide (DMF). The reaction mixture is heated at 80° C. for 7 hours and is then taken up in 200 ml of ethyl acetate. The mixture is then washed twice with 200 ml of aqueous 10% ammonia solution and then with 100 ml of water and 100 ml of saturated sodium chloride solution. The resulting solution is dried over sodium sulphate and filtered and the resulting product is concentrated under reduced pressure. The residue thus obtained is purified by chromatography on a column of silica gel, eluting under pressure with a 94/6 dichloromethane/methanol mixture. 0.54 g of (S)-N-[2-[[[4-(6-aminopyrid-3-yl)-1-[(4-ethylpiperid-3-yl)carbonyl]butyl]amino]sulphonyl]-4-bromo-6-pyrid-2-ylphenyl]propanamide is obtained in the form of an oil.

Yield (%)=30

2.3. (S)-N-[2-[[[4-(6-Aminopyrid-3-yl)-1-[(4-ethylpiperid-3-yl)carbonyl]butyl]amino]sulphonyl]-6-pyrid-2-ylphenyl]propanamide hydrochloride (2:1)

A mixture of 0.2 g (0.3 mmol) of (S)-N-[2-[[[4-(6-aminopyrid-3-yl)-1-[(4-ethylpiperid-3-yl)carbonyl]butyl]amino]sulphonyl]-4-bromo-6-pyrid-2-ylphenyl]propanamide, 0.02 g of active 10% palladium-on-charcoal and 0.2 g of ammonium formate (3.0 mmol) in 10 ml of methanol is refluxed for 2 h. The reaction mixture is filtered and is then taken up in 100 ml of dichloromethane, washed with 50 ml of saturated sodium hydrogen carbonate solution and 50 ml of saturated sodium chloride solution. The resulting solution is dried over sodium sulphate and then filtered and the resulting product is concentrated. The residue thus obtained is taken up in 40 ml of a 0.1N solution of hydrogen chloride in isopropanol and is then concentrated and purified by chromatography on an RP18 column, eluting with an acetonitrile/water gradient of from 5/95 to 30/70. 0.135 g of (S)-N-[2-[[[4-(6-aminopyrid-3-yl)-1-[(4-ethylpiperid-3-yl)carbonyl]butyl]amino]sulphonyl]-6-pyrid-2-ylphenyl]propanamide hydrochloride (2:1) is obtained.

Yield (%)=75; m.p. (°C.)=145–150;
$[\alpha]_D^{20}$ (°)=+138; (c=0.2; methanol)

EXAMPLE 3 (COMPOUND 10)

(S)-N-[2-[[[1-[(4-Ethylpiperid-3-yl)carbonyl]-4-piperid-3-ylbutyl]amino]sulphonyl]-6-thien-2-yl-phenyl]propanamide hydrochloride 3.1. Methyl (S)-α-[[(1,1-dimethylethoxy)carbonyl]amino]-1-[(phenylmethoxy)carbonyl]piperidine-4-pentanoate A mixture of 2.8 g (10.0 mmol) of methyl (S)-2-[[(1,1-dimethylethoxy)carbonyl]amino]-5-pyrid-4-ylpent-4-ynoate and 0.28 g of active 10% palladium-on-charcoal in 20 ml of ethanol is stirred for 3 hours at room temperature under 60 psi of hydrogen. The reaction mixture is filtered and concentrated under reduced pressure. The residue obtained is taken up in 20 ml of acetic acid and stirred for 14 hours in the presence of 0.05 g of platinum oxide, under 60 psi of hydrogen. The reaction mixture is filtered and then concentrated under reduced pressure. The residue obtained is taken up in 10 ml of tetrahydrofuran (THF) and 5 ml of water. This solution is cooled to 0° C., followed by addition of a solution of 3.4 g (40.0 mmol) of sodium hydrogen carbonate in 40 ml of water, and 1.63 ml (12.0 mmol) of benzyl chloroformate are added dropwise. The mixture is allowed to warm to room temperature and the reaction is continued for 4 hours. The reaction mixture is taken up in 200 ml of ethyl acetate and is washed twice with 100 ml of 1N hydrochloric acid solution and then with 100 ml of saturated sodium hydrogen carbonate solution and with 100 ml of saturated sodium chloride solution. The resulting solution is dried over sodium sulphate. The resulting product is filtered and concentrated. The residue obtained is purified by chromatography on a column of silica gel, eluting under pressure with a cyclohexane/ethyl acetate gradient of from 95/5 to 80/20. 3.55 g of methyl (S)-α-[[(1,1-dimethylethoxy)carbonyl]amino]-1-[(phenylmethoxy)carbonyl]piperidine-4-pentanoate are obtained in the form of a viscous oil.

Yield (%)=79; mp (°C.)=110.

3.2. (S)-α-[[(1,1-Dimethylethoxy)carbonyl]amino]-1-[(phenylmethoxy)carbonyl]piperidine-4-pentanoic acid A mixture of 3.55 g (8.0 mmol) of methyl (S)-α-[[(1,1-dimethylethoxy)carbonyl]amino]-1-[(phenylmethoxy)carbonyl]piperidine-4-pentanoate and 0.40 g (9.6 mmol) of lithium hydroxide monohydrate in 15 ml of methanol and 5 ml of water is stirred for 18 h at room temperature. The methanol is evaporated off under reduced pressure and the mixture is then cooled to 0° C. and acidified to pH 2 with aqueous 1N hydrochloric acid solution, and then extracted twice with 150 ml of ethyl acetate. The resulting extract is washed with 100 ml of saturated sodium chloride solution and then dried over sodium sulphate and filtered, and the residue obtained is concentrated. 3 g of (S)-α-[[(1,1-dimethylethoxy)carbonyl]amino]-1-[(phenylmethoxy)carbonyl]piperidine-4-pentanoic acid are obtained in the form of a white powder, which is used without further purification in the following step.

Yield (%)=86

3.3. Phenylmethyl (S)-4-[4-[[(1,1-dimethylethoxy)carbonyl]amino]-5-(4-ethylpiperid-1-yl)-5-oxopentyl]piperidine-1-carboxylate 1.7 g (4.4 mmol) of O-(benzotriazol-1-yl)-N,N,N',N'-tetramethyluronium hexafluorophosphate (HBTU) are added portionwise, at 0° C. under nitrogen, to a solution of 1.73 g (4.0 mmol) of (S)-α-[[(1,1-dimethylethoxy)carbonyl]amino]-1-[(phenylmethoxy)carbonyl]-piperidine-4-pentanoic acid, 0.66 g (4.4 mmol) of 4-ethylpiperidine hydrochloride and 1.8 ml (10.4 mmol) of N,N-diisopropylethylamine (DIEA) in dichloromethane. The reaction mixture is allowed to warm slowly to room temperature and the reaction is continued for 18 hours. The reaction mixture is then taken up in 200 ml of ethyl acetate and is washed with 100 ml of 1N hydrochloric acid solution and then with 100 ml of saturated sodium hydrogen carbonate solution and with 100 ml of saturated sodium chloride solution. The resulting product is dried over sodium sulphate and is filtered and then concentrated. The residue obtained is purified by chromatography on a column of silica gel, eluting under pressure with a 4/6 ethyl acetate/cyclohexane mixture. 2 g of phenylmethyl (S)-4-[4-[[(1,1-dimethylethoxy)carbonyl]amino]-5-(4-ethylpiperid-1-yl)-5-oxopentyl]piperidine-1-carboxylate are obtained in the form of a viscous oil.

Yield (%)=95

3.4. Phenylmethyl (S)-4-[4-amino-5-(4-ethylpiperid-1-yl)-5-oxopentyl]piperidine-1-carboxylate hydrochloride A solution of 1.54 g (3.0 mmol) of phenylmethyl (S)-4-[4-[[(1,1-dimethylethoxy)carbonyl]amino]-5-(4-ethylpiperid-1-yl)-5-oxopentyl]piperidine-1-carboxylate in 60 ml of dichloromethane is treated for 5 min at 0° C. with a stream of hydrogen chloride. After 3 hours at 0° C., the mixture is concentrated under reduced pressure. The resulting product is used without further purification in the following step. 1.35 g of phenylmethyl (S)-4-[4-amino-5-(4-ethylpiperid-1-yl)-5-oxopentyl]piperidine-1-carboxylate hydrochloride are thus obtained in the form of a viscous oil.

Yield (%)=100

3.5. (S)-N-[2-[[[1-[(4-Ethylpiperid-3-yl)carbonyl]-4-piperid-4-ylbutyl]amino]sulphonyl]-6-thien-2-ylphenyl]propanamide hydrochloride 1.27 g (3.3 mmol) of 2-[bis(1-oxopropyl)amino]-3-thien-2-ylbenzenesulphonyl chloride are added portionwise, at 0° C., to a solution of 1.35 g (3.0 mmol) of phenylmethyl (S)-4-[4-amino-5-(4-ethylpiperid-1-yl)-5-oxopentyl]piperidine-1-carboxylate hydrochloride and 0.96 ml (6.9 mmol) of triethylamine (TEA) in 15 ml of dichloromethane. The mixture is allowed to warm slowly to room temperature and the reaction is continued for 18 hours. The reaction mixture is taken up in 250 ml of ethyl acetate and is washed with 100 ml of 1N hydrochloric acid solution and with 100 ml of saturated sodium hydrogen carbonate solution and with 100 ml of saturated sodium chloride solution. The resulting product is dried over sodium sulphate and is filtered and then concentrated under reduced pressure. The residue obtained is taken up in 100 ml of tetrahydrofuran (THF) and is cooled to 0° C. and then treated for 5 minutes with a stream of ammonia. The mixture is allowed to warm to room temperature. After 4 hours, the reaction mixture is concentrated under reduced pressure. The residue obtained is taken up in 250 ml of ethyl acetate, washed with 50 ml of 1N hydrochloric acid solution and then with 50 ml of saturated sodium hydrogen carbonate solution and with 50 ml of saturated sodium chloride solution. The resulting product is dried over sodium sulphate and filtered and then concentrated under reduced pressure. The residue obtained is taken up in 1.2 ml of acetic acid, cooled to 0° C. and then treated with a 5N solution of hydrogen bromide in 1.2 ml of acetic acid, added dropwise. The mixture is allowed to warm to room temperature. After 4 hours, the reaction mixture is concentrated under reduced pressure. The residue obtained is taken up in 250 ml of ethyl acetate and is washed with 50 ml of saturated sodium hydrogen carbonate solution and then with 50 ml of saturated sodium chloride solution. The resulting product is dried over sodium sulphate and filtered and is then concentrated after addition of a 0.1N solution of hydrogen chloride in 40 ml of isopropanol. The residue obtained is purified by chromatography on an RP18 column, eluting with an acetonitrile/water gradient of from 5/95 to 30/70. 0.36 g of (S)-N-[2-[[[1-[(4-ethylpiperid-3-yl)carbonyl]-4-piperid-4-ylbutyl]amino]sulphonyl]-6-thien-2-ylphenyl]propanamide hydrochloride is obtained.

Yield (%)=22; m.p. (°C.)=134–138;
$[\alpha]_D^{20}$ (°)=+112 (c=0.2; methanol)

EXAMPLE 4 (COMPOUND 24)

(S)-N-[3-[[[4-(5-Aminopyrid-2-yl)-1-[[4-(difluoromethylene)piperid-1-yl]carbonyl]butyl]amino]sulphonyl]-3'-fluoro[1,1'-diphenyl]-2-yl]propanamide hydrochloride 4.1. Methyl (S)-2-[[(1,1-dimethylethoxy)carbonyl]amino]-5-(5-nitropyrid-2-yl)pent-4-ynoate A mixture of 2-bromo-5-nitropyridine (10.0 g; 49.0 mmol), methyl (S)-2-[[(1,1-dimethylethoxy)carbonyl]amino]pent-4-ynoate (13.34 g; 58.8 mmol), copper iodide (0.465 g; 2.5 mmol), potassium carbonate (13.6 g; 98.0 mmol) and dichlorobis(triphenylphosphine)palladium (1.7 g; 2.5 mmol) in 30 ml of anhydrous dimethylformamide (DMF) is heated for 4 hours at 60° C. under argon. The reaction mixture is taken up in 800 ml of ethyl acetate, washed with 2×400 ml of water, 400 ml of saturated hydrogen carbonate and 400 ml of brine, dried over sodium sulphate, filtered and then concentrated under reduced pressure. The residue obtained is purified on a column of silica, eluting with a cyclohexane/ethyl acetate gradient of from 0 to 20% ethyl acetate. 11 g of methyl (S)-2-[[(1,1-dimethylethoxy)carbonyl]amino]-5-(5-nitropyrid-2-yl)pent-4-ynoate is isolated.

Yield (%)=65

4.2. Methyl (S)-5-amino-α-[[1,1-dimethylethoxy)carbonyl]amino]pyridine-2-pentanoate A mixture of methyl (S)-2-[[(1,1-dimethylethoxy)carbonyl]amino]-5-(5-nitropyrid-2-yl)pent-4-ynoate (10.5 g; 30.0 mmol), ammonium formate (19.0 g; 300.0 mmol) and active 10% palladium-on-charcoal (1.1 g) in 100 ml of methanol is refluxed for 3 hours under argon. The reaction mixture is filtered and then concentrated under reduced pressure. The residue obtained is taken up in 400 ml of ethyl acetate, washed with 100 ml of brine, dried over sodium sulphate, filtered and then concentrated under reduced pressure. The residue is purified on a column of silica, eluting with a dichloromethane/methanol (96/4) mixture. 6.5 g of methyl (S)-5-amino-α-[[1,1-dimethylethoxy)carbonyl]amino]pyridine-2-pentanoate are isolated in the form of a viscous oil.

Yield (%)=62

4.3. (S)-5-Amino-α-[[(1,1-dimethylethoxy)carbonyl]amino]pyridine-2-pentanoic acid Lithium hydroxide monohydrate (0.9 g; 21.1 mmol) is added, at 0° C., to a mixture of methyl (S)-5-amino-α-[[1,1-dimethylethoxy)carbonyl]amino]pyridine-2-pentanoate (6.2 g; 17.6 mmol) in 45 ml of methanol and 15 ml of water. The mixture is allowed to warm slowly to room temperature and stirring is continued for 18 hours. The reaction mixture is cooled to 0° C., neutralized with 1N hydrochloric acid (22.0 ml; 22.0 mmol) and then concentrated under reduced pressure. 7.0 g of (S)-5-amino-α-[[(1,1-dimethylethoxy)carbonyl]amino]pyridine-2-pentanoic acid are isolated in the form of an amorphous powder.

Yield (%)=100

4.4. 1,1-Dimethylethyl (S)-[4-(5-aminopyrid-2-yl)-1-[[4-difluoromethylene)piperid-1-yl]carbonyl]butyl]carbamate The same procedure as in Example 1.4 is used, except for the purification on a column of silica, which is carried out with a cyclohexane/ethyl acetate gradient of from 50% to 100% ethyl acetate. Thus, starting with (S)-5-amino-α-[[(1,1-dimethylethoxy)carbonyl]amino]pyridine-2-pentanoic acid (3.14 g; 8.0 mmol) and 4-(difluoromethylene)piperidine hydrochloride (1.63 g; 9.6 mmol), 2.45 g of 1,1-dimethylethyl (S)-[4-(5-aminopyrid-2-yl)-1-[[4-difluoromethylene)piperid-1-yl]carbonyl]butyl]carbamate are obtained in the form of a white solid.

Yield (%)=72; m.p. (°C.)=142

4.5. (S)-1-[2-Amino-5-(5-aminopyrid-2-yl)-1-oxopentyl]-4-(difluoromethylene)piperidine hydrochloride The same procedure as in Example 1.5. is used. Thus, starting with 1,1-dimethylethyl (S)-[4-(5-aminopyrid-2-yl)-1-[[4-(difluoromethylene)piperid-1-yl]carbonyl]butyl]carbamate (2.4 g; 5.6 mmol), 2.25 g of (S)-1-[2-amino-5-

(5-aminopyrid-2-yl)-1-oxopentyl]-4-(difluoromethylene) piperidine hydrochloride are obtained in the form of a hygroscopic amorphous powder, which is used without further purification in the following step.

Yield (%)=100

4.6. (S)-N-[3-[[[4-(5-aminopyrid-2-yl)-1-[[4-difluoromethylene)piperid-1-yl]carbonyl]butyl]amino]sulphonyl]-3'-fluoro-[1,1'-diphenyl]-2-yl]propanamide hydrochloride The same procedure as in Example 1.6 is used, with the exception of the purification on an RP18 column, which is carried out using a water/acetonitrile gradient of from 0 to 40% acetonitrile. Thus, starting with (S)-1-[2-amino-5-(5-aminopyrid-2-yl)-1-oxopentyl]-4-(difluoromethylene) piperidine hydrochloride (0.65 g; 1.6 mmol) and [2-(bis(1-oxopropyl)amino]-3'-fluoro-1,1'-diphenyl]-3-yl]sulphonyl chloride (0.69 g; 1.6 mmol), 0.69 g of (S)-N-[3-[[[4-(5-aminopyrid-2-yl)-1-[[4-difluoromethylene)piperid-1-yl]carbonyl]butyl]amino]sulphonyl]-3'-fluoro-[1,1'-diphenyl]-2-yl]propanamide hydrochloride is isolated.

Yield (%)=65; m.p. (°C.)=136–140;
$[\alpha]_D^{20}$ (°)=+90 (c=0.2; methanol)

EXAMPLE 5 (COMPOUND 6)

(S)-N-[2-[[[4-(5-Amino-2-pyrazinyl)-1-[[4-(difluoromethylene)piperid-1-yl]carbonyl]butyl]amino]sulphonyl]-6-cyclopentylphenyl]propanamide hydrochloride 5.1. 5-Bromo-2-pyrazinamine 28.2 g of N-bromosuccinimide (0.158 mol) are added portionwise, at 0° C., to a solution of 2-aminopyrazine (15.0 g, 0.158 mol) in 900 ml of dichloromethane. After 3 hours, the reaction mixture is filtered through a sinter funnel, washed with saturated sodium carbonate (2×400 ml), water (400 ml) and brine (200 ml), dried over sodium sulphate, filtered and concentrated under reduced pressure. The residue obtained is purified on a column of silica eluted under pressure with a cyclohexane/ethyl acetate gradient (9/1) to (1/1). 18.0 g of 5-bromo-2-pyrazinamine are obtained in the form of a yellowish powder.

Yield (%)=66; m.p. (°C.)=144

5.2. Methyl (S)-5-(5-amino-2-pyrazinyl)-2-[[(1,1-dimethylethoxy)carbonyl]amino]pent-4-ynoate The process is performed in the same way as in Example 1.2., and starting with 7.5 g (43.0 mmol) of 5-bromo-2-pyrazinamine and 11.71 g (51.6 mmol) of methyl (S)-2-[[1,1-dimethylethoxy)carbonyl]amino]pent-4-ynoate, to give, after 7 h at room temperature, 10.6 g of methyl (S)-5-(5-amino-2-pyrazinyl)-2-[[(1,1-dimethylethoxy)carbonyl]amino]pent-4-ynoate in the form of a viscous oil.

Yield (%)=77

5.3. Methyl (S)-5-(5-amino-2-pyrazinyl)-2-[[(1,1-dimethylethoxy)carbonyl]amino]-pentanoate A mixture of methyl (S)-5-(5-amino-2-pyrazinyl)-2-[[(1,1-dimethylethoxy)carbonyl]amino]-pent-4-ynoate (10.0 g; 31.2 mmol), ammonium formate (29.7 g; 468.0 mmol) and active 10% palladium-on-charcoal (1.2 g) in methanol (100 ml) is refluxed for 3 hours. The reaction mixture is filtered and concentrated under reduced pressure. The residue obtained is taken up in ethyl acetate (300 ml), washed with brine (2×200 ml), dried over sodium sulphate, filtered and concentrated under reduced pressure. The residue obtained is purified on a column of silica eluted under pressure with a dichloromethane/methanol mixture (96/4). 7.9 g of methyl (S)-5-(5-amino-2-pyrazinyl)-2-[[(1,1-dimethylethoxy) carbonyl]amino]pentanoate are isolated in the form of a viscous oil.

Yield (%)=79

5.4. (S)-5-(5-Amino-2-pyrazinyl)-2-[[(1,1-dimethylethoxy)carbonyl]amino]pentanoic acid Lithium hydroxide (1.2 g, 28.6 mmol) is added, at 0° C., to a solution of methyl (S)-5-(5-amino-2-pyrazinyl)-2-[[(1,1-dimethylethoxy)carbonyl]amino]pentanoate (7.75 g, 23.9 mmol) in methanol (60 ml) and water (20 ml). The mixture is allowed to warm to room temperature and stirring is continued for 18 hours. The methanol is evaporated off under reduced pressure and the residue obtained is cooled to 0° C., acidified to pH 3–4 with 1N hydrochloric acid (30 ml), extracted with ethyl acetate (2×200 ml), washed with brine (50 ml), dried over sodium sulphate, filtered and concentrated under reduced pressure. 7.17 g of (S)-5-(5-amino-2-pyrazinyl)-2-[[(1,1-dimethylethoxy)carbonyl]amino]pentanoic acid are obtained in the form of a white powder, which is used without further purification in the following step.

Yield (%)=97; m.p. (°C.)=76.

5.5. 1,1-Dimethylethyl (S)-[4-(5-amino-2-pyrazinyl)-1-[[4-difluoromethylene)piperid-1-yl]carbonyl]butyl]carbamate The process is performed in the same way as in Example 1.4, and starting with 2.32 g (7.5 mmol) of (S)-5-(5-amino-2-pyrazinyl)-2-[[(1,1-dimethylethoxy)carbonyl]amino] pentanoic acid and 1.9 g (11.25 mmol) of 4-(difluoromethylene)piperidine hydrochloride, to give 2.61 g of 1,1-dimethylethyl (S)-[4-(5-amino-2-pyrazinyl)-1-[[4-(difluoromethylene)piperid-1-yl]carbonyl]butyl]carbamate in the form of an amorphous powder.

Yield (%)=82; m.p. (°C.)=133

5.6. (S)-1-[2-Amino-5-(5-amino-2-pyrazinyl)-1-oxopentyl]-4-(difluoromethylene)piperidine hydrochloride (2:1)

The process is performed in the same way as in Example 1.5., and starting with 2.6 g (6.1 mmol) of 1,1-dimethylethyl (S)-[4-(5-amino-2-pyrazinyl)-1-[[4-(difluoromethylene) piperid-1-yl]carbonyl]butyl]carbamate, to give 2.45 g of (S)-1-[2-amino-5-(5-amino-2-pyrazinyl)-1-oxopentyl]-4-(difluoromethylene)piperidine hydrochloride (2:1) in the form of a viscous oil.

Yield (%)=100

5.7. (S)-N-[2-[[[4-(5-Amino-2-pyrazinyl)-1-[[4-(difluoromethylene)piperid-1-yl]carbonyl]butyl]amino]sulphonyl]-6-cyclopentylphenyl]propanamide hydrochloride The process is performed in the same way as in Example 1.6, and, starting with 1.11 g (3.0 mmol) of 2-[bis(1-oxopropyl)amino]-3-cyclopentylbenzenesulphonyl chloride and 1.21 g (3.0 mmol) of (S)-1-[2-amino-5-(5-amino-2-pyrazinyl)-1-oxopentyl]-4-(difluoromethylene)piperidine hydrochloride (2:1), 1.3 g of (S)-N-[2-[[[4-(5-amino-2-pyrazinyl)-1-[[4-(difluoromethylene)piperid-1-yl]carbonyl] butyl]amino]sulphonyl]-6-cyclopentylphenyl]propanamide are obtained.

Yield (%)=68; m.p. (°C.)=136–140;
$[\alpha]_D^{20}$ (°)=+103 (c=0.2; methanol)

EXAMPLE 6 (COMPOUND 71)

N-[3-[[[(1S)-4-(5-Aminopyrid-2-yl)-1-[(4-methylpiperid-1-yl)carbonyl]butyl]amino]sulphonyl] [1,1'-diphenyl]-2-yl]acetamide hydrochloride 6.1. 2-(Diacetylamino)[1,1'-diphenyl]-3-sulphonyl chloride A solution of the N,N-diethylethanamine salt of 2-amino[1,1'-diphenyl]-3-sulphonic acid (31.2 g; 89.0 mmol) in acetic anhydride (93.0 ml) is refluxed for 4 hours. The reaction mixture is concentrated under reduced pressure. The residue obtained is taken up in dichloromethane (250.0 ml) and cooled to 0° C., followed by addition of phosphorus pentachloride (37.40 g; 178.0 mmol). After 6 hours at 0° C., the reaction mixture is concentrated under reduced pressure. The residue obtained is taken up in ether (500 ml), washed with brine (100 ml), dried over sodium sulphate, filtered and then concentrated. The residue is chromatographed on a column of Florisil®, eluting with an n-hexane/ether gradient of from 0 to 60% ether. 14.1 g of 2-(diacetylamino)[1,1'-diphenyl]-3-sulphonyl chloride are isolated in the form of an amorphous white solid.

Yield (%)=45.0

6.2. 1,1-Dimethylethyl [(S)-4-(5-aminopyrid-2-yl)-1-[(4-methylpiperid-1-yl)carbonyl]butyl]carbamate The same procedure as in Example 1.4 is used, with the exception of the purification on a column of silica, which is carried out with an ethyl acetate/methanol gradient of from 0 to 10% methanol. Thus, starting with (S)-5-amino-α-[[(1,1-dimethylethoxy)carbonyl]amino]pyridine-2-pentanoic acid (11.0 g; 31.0 mmol) and 4-methylpiperidine (5.5 ml; 46.0 mmol), 1,1-dimethylethyl [(S)-4-(5-aminopyrid-2-yl)-1-[(4-methylpiperid-1-yl)carbonyl]butyl]carbamate are isolated.

Yield (%)=86

6.3. 1-[(2S)-2-Amino-5-(5-aminopyrid-2-yl)-1-oxopentyl]-4-methylpiperidine hydrochloride The same procedure as in Example 1.5 is used. Thus, starting with 1,1-dimethylethyl [(S)-4-(5-aminopyrid-2-yl)-1-[(4-methylpiperid-1-yl)carbonyl]butyl]carbamate (10.2 g; 26.0 mmol), 9.5 g of 1-[(2S)-2-amino-5-(5-aminopyrid-2-yl)-1-oxopentyl[-4-methylpiperidine hydrochloride are obtained in the form of a hygroscopic amorphous powder, which is used without further purification in the following step.

Yield (%)=100

6.4. N-[3-[[[(1S)-4-(5-Aminopyrid-2-yl)-1-[(4-methylpiperid-1-yl)carbonyl]butyl]amino]sulphonyl][1,1'-diphenyl]-2-yl]acetamide The process is performed in the same way as in Example 1.6. Thus, starting with 2-(diacetylamino)[1,1'-diphenyl]-3-sulphonyl chloride (4.57 g; 13.0 mmol) and 1-[(2S)-2-amino-5-(5-aminopyrid-2-yl)-1-oxopentyl]-4-methylpiperidine hydrochloride, 5.2 g of N-[3-[[[(1S)-4-(5-aminopyrid-2-yl)-1-[(4-methylpiperid-1-yl)carbonyl]butyl]amino]sulphonyl][1,1-diphenyl]-2-yl]acetamide are obtained.

Yield (%)=66; m.p. (°C.)=176–180;

$[\alpha]_D^{20}$ (°)=+184 (c=0.2; methanol)

EXAMPLE 7 (COMPOUND 52)

N-[[[3-[(1S)-4-(5-aminopyrid-2-yl)-1-[[4-(difluoromethylene)piperid-1-yl]carbonyl]butyl]amino]sulphonyl][1,1'-diphenyl]-2-yl]acetamide hydrochloride The process is performed in the same way as in Example 1.6. Thus, starting with 3.52 g (10.0 mmol) of 2-(diacetylamino)[1,1'-diphenyl]-3-sulphonyl chloride and 4.2 g (10.5 mmol) of 1,1-dimethylethyl (S)-[4-(5-aminopyrid-2-yl)-1-[[4-difluoromethylene)piperid-1-yl]carbonyl]butyl]carbamate, 4.5 g of N-[[[3-[(1S)-4-(5-aminopyrid-2-yl)-1-[[4-(difluoromethylene)piperid-1-yl]carbonyl]butyl]amino]sulphonyl][1,1'-diphenyl]-2-yl]acetamide are obtained.

Yield (%)=71; m.p. (°C.)=170–174;

$[\alpha]_D^{20}$ (°)=+90 (c=0.2; methanol)

EXAMPLE 8 (COMPOUND 114)

N-[3-[[[(1S)-4-(6-aminopyrid-3-yl)-1-[(4-methylpiperid-1-yl)carbonyl]butyl]amino]sulphonyl]-5-phenylpyrid-4-yl]propanamide hydrochloride 8.1 1,1-Dimethylethyl (3,5-dibromopyrid-4-yl)carbamate A mixture of 1,1-dimethylethyl 4-pyridinecarbamate (11.0 g; 57.0 mmol) and N-bromo-succinimide (25.6 g; 142.0 mmol) in acetonitrile (50 ml) is heated for 12 hours at 55° C. The reaction mixture is concentrated under reduced pressure. The residue obtained is taken up in ether (400 ml), washed with saturated aqueous potassium bicarbonate solution (2×200 ml), dried over sodium sulphate, filtered and then concentrated under reduced pressure. The residue is chromatographed on a column of silica, eluting with an ethyl acetate/cylohexane gradient of from 0 to 10% ethyl acetate. 8.2 g of 1,1-dimethylethyl (3,5-dibromopyrid-4-yl) carbamate are isolated in the form of a white solid.

Yield (%)=41

8.2 1,1-Dimethylethyl (3-bromo-5-phenylpyrid-4-yl) carbamate

A mixture of 1,1-dimethylethyl (3,5-dibromo-4-pyridyl) carbamate (4.2 g; 12.0 mmol), phenylboronic acid (1.76 g; 14.4 mmol), sodium carbonate (3.1 g; 29.2 mmol) and tetrakis(triphenylphosphine)palladium (0) (0.416 g; 0.36 mmol) in dioxane (24 ml) and water (12 ml) is heated at 70° C. under argon for 8 hours. The reaction mixture is concentrated under reduced pressure. The residue obtained is taken up in ethyl acetate (200 ml), washed with water (2×100 ml) and brine (100 ml), dried over sodium sulphate, filtered and then concentrated under reduced pressure. The residue is chromatographed on a column of silica, eluting with an ethyl acetate/cyclohexane gradient of from 0 to 5%. 2.3 g of 1,1-dimethylethyl (3-bromo-5-phenylpyrid-4-yl)carbamate are isolated in the form of a white solid.

Yield (%)=55

8.3 Tributyl[(phenylmethyl)thio]stannane 1,8-Diazabicyclo[5.4.0.]undec-7-ene (DBU) is added dropwise at 20° C., under argon, to a solution of benzenemethanethiol (11.72 ml; 100.0 mmol) in anhydrous DMF (20.0 ml). After 0.5 hour at 20° C., the reaction mixture is cooled to 0° C. and tributyltin chloride is added dropwise. The mixture is allowed to warm to room temperature and stirring is continued for 5 hours. The reaction mixture is taken up in pentane (400 ml), washed with water (3×300 ml) and brine (100 ml), washed with sodium sulphate, filtered and then concentrated under reduced pressure. 39.0 g of tributyl[(phenylmethyl)thio]stannane are obtained in the form of a colourless oil, which is used without further purification in the following step.

Yield (%)=95

8.4 1,1-Dimethylethyl [3-phenyl-5-[(phenylmethyl)thio] pyrid-4-yl]carbamate

A mixture of 1,1-dimethylethyl (3-bromo-5-phenylpyrid-4-yl)carbamate (2.30 g; 6.6 mmol), tributyl[(phenylmethyl) thio]stannane (2.44 ml; 7.3 mmol) and tetrakis (triphenylphosphine)palladium (0) (0.30 g; 0.26 mmol) in anhydrous dioxane (4.0 ml) is heated for 10 hours under argon at 90° C. After 4 hours and 6 hours, tetrakis (triphenylphosphine)palladium (0) is added (0.30 g and 0.15 g, respectively). The reaction mixture is taken up in ether (100 ml), treated for 0.5 hour with aqueous 5% potassium fluoride solution (50 ml) and then filtered through a sinter funnel. The filtrate is washed with brine (50 ml), dried over sodium sulphate, filtered and then concentrated without reduced pressure. The residue obtained is chromatographed on a column of silica, eluting with an ethyl acetate/ cyclohexane gradient of from 0 to 20% ethyl acetate. 1.0 g of 1,1-dimethylethyl[3-phenyl-5-[(phenylmethyl)thio] pyrid-4-yl]carbamate are isolated in the form of a white solid.

Yield (%)=45

8.5 3-Phenyl-5-[(phenylmethyl)thio]pyrid-4-amine

A solution of 1,1-dimethylethyl [3-phenyl-5-[(phenylmethyl)thio]pyrid-4-yl]carbamate (0.9 g; 2.7 mmol) in methanol (50 ml) is treated for 5 minutes at 0° C. with a stream of hydrogen chloride. The mixture is allowed to warm to room temperature and stirring is continued for 6 hours. The reaction mixture is concentrated under reduced pressure. The residue obtained is taken up in ethyl acetate (150 ml), treated with saturated aqueous potassium carbonate solution (20 ml), dried over sodium sulphate and filtered and then concentrated under reduced pressure. 0.8 g of 3-phenyl-5-[(phenylmethyl)thio]pyrid-4-amine is obtained in the form of a viscous oil, which is used without further purification in the following step.

Yield (%)=100

8.6 4-[bis(1-oxopropyl)amino]-5-phenylpyrid-3-sulphonyl chloride

A solution of 3-phenyl-5-[(phenylmethyl)thio]pyrid-4-amine (0.8 g; 2.74 mmol) in propionic anhydride is heated at 150° C. for 6 hours. The reaction mixture is concentrated under reduced pressure and used without further purification in the following step. Sulphuryl chloride (0.75 ml; 9.4 mmol) is added dropwise, at 5° C., to a mixture of the crude product obtained above in acetic acid (3 ml) and water (0.2 ml). After 0.5 hour at 5° C., the reaction mixture is concentrated under reduced pressure. The residue obtained is taken up in ether (150 ml), washed with water (50 ml) and brine (50 ml), dried over sodium sulphate, filtered and then concentrated under reduced pressure. 1.1 g of 4-[bis(1-oxopropyl)amino]-5-phenylpyrid-3-sulphonyl chloride are obtained in the form of a viscous oil, which is used without further purification in the following step.

Yield (%)=100

8.7 N-[3-[[[(1S)-4-(6-aminopyrid-3-yl)-1-[(4-methylpiperid-1-yl)carbonyl]butyl]amino]sulphonyl]-5-phenylpyrid-4-yl]propanamide hydrochloride A solution of 4-[bis(1-oxopropyl)amino]-5-phenylpyrid-3-sulphonyl chloride (0.5 g; ~1.0 mmol) in dichloromethane (3 ml) is added dropwise, at 0° C., to a mixture of 1-[(2S)-2-amino-5-(6-aminopyrid-3-yl)-1-oxopentyl]-4-methylpiperidine (0.35 g; 1.1 mmol) and triethylamine (0.45 ml; 3.3 mmol) in dichloromethane (3 ml). After 6 hours at 0° C., the reaction mixture is taken up in ethyl acetate (100 ml), washed with brine (50 ml), dried over sodium sulphate, filtered and then concentrated under reduced pressure. The residue obtained is taken up in tetrahydrofuran (20.0 ml), cooled to 0° C. and then treated for 5 minutes with a stream of ammonia gas. After 4 hours at room temperature, the reaction mixture is concentrated under reduced pressure. The residue is chromatographed on a column of silica, eluting with a dichloromethane/methanol gradient of from 0 to 5% methanol. 0.45 g of base is isolated (yield (%)=77), which is taken up in 2 ml of a 0.1N solution of hydrogen chloride in isopropanol and is concentrated under reduced pressure. The residue is purified by chromatography on a column of RP18 silica gel, eluting with a 3/7 acetonitrile/water mixture. 0.42 g of N-[3-[[[(1S)-4-(6-aminopyrid-3-yl)-1-[(4-methylpiperid-1-yl)carbonyl]butyl]amino] sulphonyl]-5-phenylpyrid-4-yl]propanamide hydrochloride is isolated.

Yield (%)=66; m.p. (°C.)=180–184;

$[\alpha]_D^{20}$ (°)=+100 (c=0.2; methanol)

EXAMPLE 9 (COMPOUND 118)

[1,1'-diphenyl]-3-sulphonamide, N-[(1S)-4-(5-amino-2-pyridyl)-1-[[4-difluoromethylene)-1-piperidyl]carbonyl]butyl]-2-(formylamino)-3'-methyl hydrochloride 9.1 [1,1'-diphenyl]-3-sulphonamide-2-amino-N-[(1S)-4-(5-amino-2-pyridyl)-1-[[4-difluoromethylene)-1-piperidyl]carbonyl]butyl]-3'-methyl 0.74 ml of triethylamine (5.31 mmol) is added dropwise to a stirred solution of 0.64 g (1.77 mmol) of (1S)-5-amino-α-[[4-difluoromethylene)-1-piperidyl]carbonyl]-2-pyridinebutanamine dihydrochloride in 10 ml of dichloromethane, followed by dropwise addition, at 0° C., of a solution of 2-amino-3'-methyl-[1,1'-diphenyl]-3-sulphonyl chloride (0.50 g; 1.77 mmol) in 2 ml of dichloromethane. After stirring for 16 h at room temperature, the reaction medium is evaporated under reduced pressure. The residue is taken up in 100 ml of ethyl acetate and washed with 25 ml of saturated sodium bicarbonate solution and then with 25 ml of saturated sodium chloride solution and finally dried over Na$_2$SO$_4$. The solvent is evaporated off under reduced pressure and the residue is chromatographed on silica in a dichloromethane/methanol mixture of from 0 to 10% methanol, to give 0.6 g of pure product.

Yield (%)=60

9.2 N-[(1S)-4-(5-amino-2-pyridyl)-1-[[4-difluoromethylene)-1-piperidyl]carbonyl]butyl]-2-(formylamino)-3'-methyl[1,1'-diphenyl]-3-sulphonamide hydrochloride A solution of 0.55 g of N-[(1S)-4-(5-amino-2-pyridyl)-1-[[4-difluoromethylene)-1-piperidyl]carbonyl]butyl]-2-(formylamino)-3'-methyl 2-N-amino-[1,1'-diphenyl]-3-sulphonamide (1 mmol) in 3 ml of ethyl orthoformate is heated at 125° C. with stirring and under argon for 7 h. The reaction medium is then poured into a solution of 50 ml of acetic acid and 50 ml of water and heated at 100° C. for 1 h. After evaporation under reduced pressure, the residue is taken up in 100 ml of ethyl acetate, washed with 50 ml of saturated sodium chloride solution and dried over Na$_2$SO$_4$. The solvent is evaporated off under reduced pressure and the residue is taken up in 10 ml of a 0.1 N solution of hydrogen chloride in isopropanol and evaporated under reduced pressure. The product is then chromatographed on RP18 silica in an N/100 hydrochloric acid/acetonitrile mixture of from 0 to 100% acetonitrile. 0.22 g of the desired product is thus obtained.

Yield (%)=37; m.p. (°C.)=168;

$[\alpha]_D^{20}$ (°)=+108 (c=0.2; methanol)

EXAMPLE 10 (COMPOUND 123)

N-[2-[[[(1S,3Z)-4-(5-amino-2-pyridyl)-1-[[4-difluoromethylene)-1-piperidyl]carbonyl]-3-butenyl]amino]sulphonyl]-6-(2-thienyl)phenyl]acetamide hydrochloride 10.1 Methyl (2S)-2-[2,2-dimethyl-1-oxopropoxy)amino]-5-nitro-2-pyridyl)-4-pentynoate 18.3 ml (105.2 mmol) of diisopropylethylamine are added to a solution of 11.95 g (52.6 mmol) of methyl (2S)-2-[(2,2-dimethyl-1-oxopropoxy)amino]-4-pentynoate and 10 g (63.1 mmol) of 2-chloro-5-nitropyridine in 100 ml of dichloromethane, followed by addition of 380 mg (2.6 mmol) of copper bromide. The medium is degassed by bubbling argon through for 15 min. 740 mg (1.05 mmol) of tetrakis(triphenylphosphine)palladium (0) are added, under argon, to the reaction medium which is then refluxed (temperature=40° C.) for 4 h. The medium turns black. The dichloromethane is evaporated off and the residue is then taken up in 500 ml of ethyl acetate. The organic phase is washed with saturated sodium chloride solution, dried over anhydrous sodium sulphate and then evaporated to dryness. The evaporation residue is purified on silica with a cyclohexane/ethyl acetate mixture (85/15). 16.6 g of a brown powder are obtained.

Yield (%)=90

10.2 Methyl (2S)-5-(5-amino-2-pyridyl)-2-[(2,2-dimethyl-1-oxopropoxy)amino]-4-pentynoate A mixture of 11.6 g (33.2 mmol) of methyl (2S)-2-[(2,2-dimethyl-1-oxopropoxy)amino]-5-nitro-2-pyridyl)-4-pentynoate, 6.5 g (116.2 mmol) of iron, 100 ml of water, 200 ml of ethanol and 20 ml of acetic acid is refluxed for 5 h. The ethanol is evaporated off and the medium is then filtered through Celite. The product is extracted with dichloromethane. The organic phase is dried over anhydrous magnesium sulphate and then evaporated to dryness. The evaporation residue is purified on silica with a dichloromethane/methanol mixture (97/3). 8 g of a brown oil are obtained.

Yield (%)=80

10.3 Methyl (2S,4Z)-5-(5-amino-2-pyridyl)-2-[(2,2-dimethyl-1-oxopropoxy)amino]-4-pentenoate 4 g (12.5 mmol) of methyl (2S,4Z)-5-(5-amino-2-pyridyl)-2-[(2,2-dimethyl-1-oxopropoxy)amino]-4-pentynoate dissolved in 100 ml of ethyl acetate are placed in Parr apparatus and hydrogenated at room temperature at a pressure of 8 psi, for 4 h. The mixture is filtered through Whatman paper and the filtrate is evaporated. The crude residue is purified on silica with a cyclohexane/ethyl acetate mixture (1/1). 1.8 g of a light brown powder are obtained.

Yield (%)=45

10.4 (2S,4Z)-5-(5-amino-2-pyridyl)-2-[(2,2-dimethyl-1-oxopropoxy)amino]-4-pentenoic acid 260 mg of lithium hydroxide (6.16 mmol) are added to a solution of methyl (2S,4Z)-5-(5-amino-2-pyridyl)-2-[(2,2-dimethyl-1-oxopropoxy)amino]-4-pentenoate (1.8 g, i.e. 5.6 mmol) in a methanol/water mixture (45/15). The mixture is left stirring overnight at room temperature. The medium is evaporated to dryness by azeotropic distillation of the toluene. 1.6 ml of 4N hydrogen chloride in dioxane and 30 ml of dichloromethane are added to the medium. The resulting medium is again evaporated to dryness. The expected compound is obtained quantitatively in the form of an orange gum.

10.5 6-(1Z,4S)-5-[4-(difluoromethylene)-1-piperidyl]-4-[2,2-dimethyl-1-oxopropoxy)amino]-5-oxo-1-pentenyl-3-pyridinamine 2.82 ml (16.1 mmol) of diisopropylethylamine are added, under argon, to a solution of 1.07 g (6.2 mmol) of 4-difluoromethylenepiperidine in a dichloromethane/dimethylformamide mixture (8/2). The medium is cooled to 0° C. At this temperature, 2.2 g (6.2 mmol) of (2S,4Z)-5-(5-amino-2-pyridyl)-2-[(2,2-dimethyl-1-oxopropoxy)amino]-4-pentenoic acid and 2.2 g (6.93 mmol) of TBTU are added. The mixture is allowed to warm to room temperature with stirring overnight. The medium is evaporated to dryness and the residue is taken up in ethyl acetate and washed with saturated sodium carbonate solution. The organic phase is dried over anhydrous sodium sulphate and evaporated to dryness. The evaporation residue is purified on silica with a cyclohexane/ethyl acetate/methanol mixture (45/45/10).

Yield (%)=75.

10.6 N-[2-[[[(1S,3Z)-4-(5-amino-2-pyridyl)-1-[[4-difluoromethylene)-1-piperidyl]carbonyl]-3-butenyl]amino]sulphonyl]-6-(2-thienyl)phenyl]acetamide hydrochloride 46 mmol (11.5 ml) of 4N hydrogen chloride in dioxane are added to a solution of 1.95 g (4.6 mmol) of 6-(1Z,4S)-5-[4-(difluoromethylene)-1-piperidyl]-4-[2,2-dimethyl-1-oxopropoxy)amino]-5-oxo-1-pentenyl-3-pyridinamine in 40 ml of dichloromethane. The medium is left stirring overnight at room temperature. The medium is evaporated to dryness. 351 mg (0.98 mmol) of the residue are taken up in 3 ml of dichloromethane and 401 µl (2.94 mmol) of triethylamine are added thereto. The medium is cooled to 0° C. At this temperature, 350 mg (0.98 mmol) of 2-[(diacetylamino)-1,1'-diphenyl]-3-sulphonyl chloride are added. The mixture is allowed to warm to room temperature with stirring over 1 h. The medium is washed with aqueous sodium chloride solution and then evaporated to dryness. The residue is taken up in 5 ml of tetrahydrofuran. Ammonia is bubbled through the medium, cooled to 0° C., for 45 min. The tetrahydrofuran is evaporated off and the product is then purified on silica with a cyclohexane/ethyl acetate mixture (3/7) and then on a reverse phase using an N/100 hydrochloric acid/acetonitrile gradient of from 0% to 100% acetonitrile.

Yield (%)=20; m.p. (°C.)=170;

$[\alpha]_D^{20}$ (°)=+40 (c=0.2; methanol)

EXAMPLE 11 (COMPOUND 121)

N-[3-[[[(1S,3E)-4-(5-amino-2-pyridyl)-1-[[4-difluoromethylene)-1-piperidyl]carbonyl]-3-butenyl]amino]sulphonyl[1,1'-diphenyl]-2-yl-acetamide hydrochloride 11.1 Methyl (2S)-2-[(triphenylmethylamino]-4-pentynoate 22 ml (88 mmol) of 4N hydrogen chloride in dioxane are added to a solution of 2 g (8.8 mmol) of methyl (S)-2-[[1,1-dimethylethoxy)carboxy]amino]pent-4-ynoate in 5 ml of dichloromethane. The mixture is left stirring for 2 h at room temperature. The medium is evaporated to dryness and then taken up in 8 ml of dichloromethane. 1.8 ml (13.2 mmol) of triethylamine are added thereto. The medium is cooled to 0° C. At this temperature, 2.6 g (0.65 mmol) of trityl chloride are added thereto. The mixture is allowed to warm to room temperature with stirring overnight. The medium is washed with water, dried over anhydrous sodium sulphate and then evaporated to dryness. The evaporation residue is purified on silica with a cyclohexane/ethyl acetate mixture (9/1). 3 g of a viscous white solid are obtained.

Yield (%)=92.

11.2 Methyl (2S)-5-(tributylstannyl)-2-[(triphenylmethyl)amino]-4-pentenoate

Argon is bubbled through a solution of 200 mg (0.54 mmol) of methyl (2S)-2-[(triphenylmethylamino]-4-pentynoate in 2 ml of anhydrous tetrahydrofuran, for 10 min. 5% tetrakis(triphenylphosphine)palladium (0) (3 mg; 2.7× 10⁻³ mmol) is added. When the medium is homogeneous, it is cooled to 0° C. 173 µl (0.65 mmol) of tributyltin hydride are added dropwise at 0° C., under argon. The medium turns an opaque yellow. The medium is allowed to warm to room temperature with stirring over 2 h. The medium is evaporated to dryness and then purified on Florisil®, eluting with pure cyclohexane. A transparent viscous liquid is obtained.

11.3 Methyl (2S,4E)-5-(5-nitro-2-pyridyl)-2-[(triphenylmethyl)amino]-4-pentenoate Argon is bubbled through a solution of 80 mg (0.13 mmol) of methyl (2S)-5-(tributylstannyl)-2-[(triphenylmethyl)amino]-4-pentenoate and 39.5 mg (0.19 mmol) of 2-bromo-5-nitropyridine in 1 ml of anhydrous dioxane, for 10 min. 11.4 mg (0.0125 mmol) of tetrakis (triphenylphosphine)palladium (0) are then added. The medium is maintained at 110° C. for 24 h, under argon. The medium is washed with saturated potassium fluoride solution and then extracted with ethyl acetate. The organic phase is dried over anhydrous sodium sulphate and then concentrated under reduced pressure. The evaporation residue is purified on silica with a 98/2 and then 95/5 cyclohexane/ethyl acetate mixture. 20 mg of a yellow oil are obtained.

Yield (%)=31.

11.4 Methyl (2S,4E)-5-(5-amino-2-pyridyl)-2-[(triphenylmethyl)amino]-4-pentenoate A mixture of 1.2 g (2.43 mmol) of methyl (2S,4E)-5-(5-nitro-2-pyridyl)-2-[(triphenylmethyl)amino]-4-pentenoate, 477 mg (8.5 mmol) of iron, 3.6 ml of water, 7.2 ml of ethanol and 720 μl of acetic acid is maintained at 110° C. for 40 min. The medium is filtered through Celite. The ethanol is evaporated off under reduced pressure. The crude residue is extracted with a dichloromethane/isopropanol mixture (75/25). The organic phase is dried over anhydrous sodium sulphate and then concentrated under reduced pressure. The evaporation residue is purified on silica with a cyclohexane/ethyl acetate mixture (6/4). 500 mg of a yellow oil are obtained.

Yield (%)=41.6.

11.5 Methyl (2S,4E)-2-[(2,2-dimethyl-1-oxopropoxylamino]-5-[5-[2,2-dimethyl-1-oxopropyl)amino]-2-pyridyl]-4-pentenoate A solution of 500 mg (1.08 mmol) of methyl (2S,4E)-5-(5-amino-2-pyridyl)-2-[(triphenylmethyl)amino]-4-pentenoate in 3.24 ml of hydrochloric acid and 2 ml of tetrahydrofuran is refluxed at 65° C. for 1 h 30 min. The medium is allowed to cool. 1N sodium hydroxide is added to the medium until the pH is basic. 2.35 g (10.8 mmol) of di-tert-butyl carbonate are added thereto. The medium is left stirring at room temperature for 24 h. The medium is washed with diethyl ether and then re-acidified with citric acid and the crude product is extracted with dichloromethane. The organic phase is dried over anhydrous sodium sulphate and then evaporated to dryness. 300 mg of a yellow oil are obtained.

Yield (%)=60.

11.6 N-(1S,3E)-1-[[4-difluoromethylene)-1-piperidyl]carbonyl]-4-[5-(2,2-dimethyl-1-oxopropyl)amino]-2-pyridyl]-3-butenyl]-2,2-dimethylpropanamide 300 mg (0.73 mmol) of methyl (2S,4E)-2-[(2,2-dimethyl-1-oxopropylamino]-5-[5-[2,2-dimethyl-1-oxopropyl)amino]-2-pyridyl]-4-pentenoate are added to a solution, cooled to 0° C., of 120 mg (0.73 mmol) of 4-difluoromethylenepiperidine in 8 ml of dichloromethane and 509 μl of diisopropylethylamine, followed by addition of 257 mg (0.80 mmol) of TBTU. The medium is left stirring at 0° C. for 2 h 30 min. The dichloromethane is evaporated off. The residue is taken up in ethyl acetate, washed with saturated sodium carbonate solution and then with water, and dried over anhydrous sodium sulphate. The organic phase is concentrated under vacuum. The evaporation residue is purified on silica with a dichloromethane/methanol mixture (99/1). 342 mg of a yellow oil are obtained.

Yield (%)=89.7.

11.7 N-[3-[[[(1S,3E)-4-(5-amino-2-pyridyl)-1-[[4-difluoromethylene)-1-piperidyl]carbonyl]-3-butenyl]amino]sulphonyl][1,1'-diphenyl]-2-yl-acetamide hydrochloride 4.6 ml (6.6 mmol) of 4N hydrogen chloride in dioxane are added to a solution of 342 mg (0.66 mmol) of N-(1S,3E)-1-[[4-difluoromethylene)-1-piperidyl)carbonyl]-4-[5-(2,2-dimethyl-1-oxopropyl)amino]-2-pyridyl]-3-butenyl]-2,2-dimethylpropanamide in 4 ml of dichloromethane. The medium is stirred at room temperature for 2 h. The medium is evaporated to dryness. The evaporation residue is taken up in 3 ml of dichloromethane. 315 μl (2.31 mmol) of triethylamine are added thereto. The medium is cooled to 0° C. At this temperature, 232 mg (0.66 mmol) of 2-(diacetylamino)-[1,1-diphenyl]-3-sulphonyl chloride are added. The medium is allowed to warm to room temperature with stirring over 2 h. The medium is washed with saturated sodium chloride solution. The organic phase is dried over anhydrous sodium sulphate and then evaporated to dryness. The residue is taken up in 4 ml of tetrahydrofuran and cooled to 0° C. Ammonia is bubbled through over 45 min at 0° C. The mixture is evaporated to dryness. The evaporation residue is purified on silica with a cyclohexane/ethyl acetate mixture (2/8) and then on a reverse phase using an N/100 hydrochloric acid/acetonitrile gradient of from 0 to 100% acetonitrile. 150 mg of the expected compound are obtained.

Yield (%)=38; m.p. (°C.)=175;

$[\alpha]_D^{20}$ (°)=+76 (c=0.1; methanol)

EXAMPLE 12 (COMPOUND 126)

(S)-N-[3-[[[3-(5-amino-2-pyridyl)-1-[[4-(difluoromethylene)-1-piperidyl]carbonyl]propyl]amino]sulphonyl][1,1'-diphenyl]-2-yl]acetamide hydrochloride 12.1 Phenylmethyl (S)-4-iodo-2-[[(phenylmethoxy)carbonyl]amino]butanoate 14 g (43 mmol) of di(acetyloxy)iodobenzene and 10.5 g (41 mmol) of iodine are added to a solution of 30 g (80 mmol) of 1-phenylmethyl (L)-(N)-[(phenylmethoxy)carbonyl]glutamate in 800 ml of carbon tetrachloride, under argon. The mixture is refluxed under UV irradiation. After 1 h 30 min, a further 14 g (43 mmol) of di(acetyloxy)iodobenzene and 10.5 g of iodine are added. After UV irradiation for 2 h, the mixture is washed with 10% sodium hydrogen sulphite solution (2×300 ml), then with 200 ml of saturated sodium hydrogen carbonate solution and then with 200 ml of water. The mixture is dried over sodium sulphate, concentrated under reduced pressure and purified by filtration through a column of silica gel, eluting with a 95/5 cyclohexane/ethyl acetate mixture. 12.8 g of phenylmethyl (S)-4-iodo-2-[[(phenylmethoxy)carbonyl]amino]butanoate are obtained in the form of an oil.

Yield (%)=35.

12.2 Phenylmethyl (S)-5-nitro-α-[[(phenylmethoxy)carbonyl]amino]-2-pyridinebutanoate A suspension of 6 g (92 mmol) of zinc powder and 0.4 ml (4.7 mmol) of 1,2-dibromoethane in 7 ml of anhydrous N,N-dimethylformamide is heated at 60° C. with stirring and under argon for 45 min. 0.126 ml (1 mmol) of trimethylsilyl chloride is then added and the mixture is stirred vigorously at room temperature for 30 min. A solution of 7 g (15.4 mmol) of phenylmethyl (S)-4-iodo-2-[[(phenylmethoxy)carbonyl]amino]butanoate in 1 ml of anhydrous N,N-dimethylformamide is then added. After 30 min at room temperature, 0.28 g (0.31 mmol) of tris(dibenzylideneacetone)dipalladium (0), 0.38 g (1.24 mmol) of tri-ortho-tolylphosphine, 3.78 g (18.5 mmol) of 2-bromo-5-nitropyridine and 1 ml of anhydrous N,N-dimethylformamide are added at room temperature and the mixture is stirred for 3 h at room temperature. The reaction medium is taken up in 200 ml of ethyl acetate and 5 g of active charcoal and then filtered through a cake of Celite. The cake is rinsed with 2×100 ml of ethyl acetate and the organic phases are combined, washed with 5×100 ml of water, dried over sodium sulphate and concentrated under reduced pressure. The residue is purified by filtration on a column of silica gel, eluting with a cyclohexane/ethyl acetate gradient of from 0 to 20% ethyl acetate. 5.16 g of phenylmethyl (S)-5-nitro-α-[[(phenylmethoxy)carbonyl]amino]-2-pyridinebutanoate are thus obtained in the form of a yellow foam.

Yield (%)=74.

12.3 (S)-α,5-diamino-2-pyridinebutanoic acid

A mixture of 5.16 g (11.5 mmol) of phenylmethyl (S)-5-nitro-α-[[(phenylmethoxy)carbonyl]amino]-2-pyridinebutanoate, 2 g of active charcoal and 0.77 g of active palladium-on-charcoal in 100 ml of methanol and 100 ml of water is stirred for 4 days at 50 psi of hydrogen at room temperature. The reaction medium is filtered through a cake of Celite and the cake is rinsed with 3×50 ml of boiling water. The aqueous phases are combined and concentrated under reduced pressure. 2.05 g of (S)-α,5-diamino-2-pyridinebutanoic acid are thus obtained in the form of a white solid.

Yield (%)=92; m.p. (°C.) >260.

12.4 (S)-α,5-bis[[(1,1-dimethylethoxy)carbonyl]amino]-2-pyridinebutanoic acid 1.05 ml (9.19 mmol) of aqueous 35% sodium hydroxide solution and 2 g (9.17 mmol) of bis(1,1-dimethylethyl) dicarbonate are added to a solution of 0.85 g (4.36 mmol) of (S)-α,5-diamino-2-pyridinebutanoic acid in 50 ml of water and 50 ml of 1,1-dimethylethanol. The solution is stirred for 2 h at room temperature and a further 2 g (9.17 mmol) of bis(1,1-dimethylethyl) dicarbonate and 1 ml of aqueous 35% sodium hydroxide solution are added. After stirring for 15 h at room temperature, the reaction medium is diluted with 100 ml of aqueous 1N sodium hydroxide solution and 50 ml of saturated sodium chloride solution and then washed with 2×300 ml of ether. The aqueous phase is acidified with citric acid to pH=4–5 and then extracted with a 75/25 dichloromethane/isopropanol mixture (2×100 ml). The organic phases are combined and concentrated under reduced pressure. The residue is taken up in 100 ml of toluene and concentrated again under reduced pressure. 1.18 g of (S)-α,5-bis[[(1,1-dimethylethoxy)carbonyl]amino]-2-pyridinebutanoic acid are obtained in the form of a viscous oil.

Yield (%)=69

12.5 1,1-dimethylethyl (S)-1-[[4-(difluoromethylene)-1-piperidyl]carbonyl]-3-[5-[[(1,1-dimethylethoxy)carbonyl]amino]2-pyridyl]propyl]carbamate 1.16 g (3.6 mmol) of O-(1-benzotriazolyl)-N,N,N',N'-tetramethyluronium tetrafluoroborate (TBTU) are added, under argon and with stirring at 0° C., to a mixture of 1.18 g (3 mmol) of (S)-α,5-bis[[(1,1-dimethylethoxy)carbonyl]amino]-2-pyridinebutanoic acid, 1.15 ml (6.6 mmol) of N,N-diisopropylethylamine and 0.56 g (3.3 mmol) of 4-difluoromethylene-1-piperidine hydrochloride in 30 ml of dichloromethane. The mixture is allowed to warm to room temperature and stirring is continued for 2 h. The reaction medium is diluted with 50 ml of dichloromethane and washed with 50 ml of water and then with 50 ml of saturated sodium hydrogen carbonate solution and again with 2×50 ml of water. The organic phase is dried over sodium sulphate and concentrated under reduced pressure, and the residue is purified by chromatography on a column of silica gel, eluting with a 1/1 cyclohexane/ethyl acetate mixture. 1.62 g of 1,1-dimethylethyl (S)-1-[[4-(difluoromethylene)-1-piperidyl]carbonyl]-3-[5-[[(1,1-dimethylethoxy)carbonyl]amino]2-pyridyl]propyl]carbamate are obtained in the form of a viscous oil.

Yield (%)=100

12.6 (S)-5-amino-α-[[4-(difluoromethylene)-1-piperidyl]carbonyl]-2-pyridinepropanamine hydrochloride A solution of 1.62 g (3.18 mmol) of 1,1-dimethylethyl (S)-1-[[4-(difluoromethylene)-1-piperidyl]carbonyl]-3-[5-[[(1,1-dimethylethoxy)carbonyl]amino]2-pyridyl]propyl]carbamate in 50 ml of dichloromethane is treated for 5 min at 0° C. with a stream of hydrogen chloride. The solution is allowed to warm to room temperature and stirring is continued for 3 h. The white precipitate obtained is then filtered off and rinsed with 10 ml of dichloromethane. 1 g of highly hygroscopic (S)-5-amino-α-[[4-(difluoromethylene)-1-piperidyl]carbonyl]-2-pyridinepropanamine hydrochloride (2:1) is thus obtained, and is used without further purification in the following step.

Yield (%)=88; m.p. (°C.)=70

12.7 (S)-N-[3-[[[3-(5-amino-2-pyridyl)-1-[[4-(difluoromethylene)-1-piperidyl]carbonyl]propyl]amino]sulphonyl][1,1'-diphenyl]-2-yl]acetamide hydrochloride 0.8 ml (5.7 mmol) of triethylamine is added to a solution of 0.7 g (1.83 mmol) of (S)-5-amino-α-[[4-(difluoromethylene)-1-piperidyl]carbonyl]-2-pyridinepropanamine hydrochloride (2:1) in 20 ml of dichloromethane, and the resulting solution is cooled to 0° C. with stirring. 0.58 g (1.64 mmol) of 2-(diacetylamino)-[1,1'-diphenyl]-3-sulphonyl chloride is then added portion-wise. After 2 h at 0° C., 50 ml of dichloromethane are added and the solution is washed successively with 2×20 ml of water, 50 ml of saturated sodium hydrogen carbonate solution and 2×10 ml of water. The organic phase is dried over sodium sulphate and concentrated under reduced pressure. The residue obtained is taken up in 20 ml of tetrahydrofuran and is then cooled to 0° C. and treated for 5 min with a stream of ammonia. The reaction mixture is allowed to warm to room temperature and, after 4 h, is then concentrated under reduced pressure. The residue obtained is purified by chromatography on a column of silica gel, eluting under pressure with a 99/1 dichloromethane/methanol mixture. After concentration under reduced pressure, the residue is then taken up in 1.8 ml of a 1M solution of hydrogen chloride in methanol (1.8 mmol) and is again concentrated under reduced pressure and then purified by chromatography on an RP18 column, eluting with an acetonitrile/N/1000 hydrochloric acid gradient of from 5/95 to 100/0 over 60 min. After lyophilization, 0.61 g of (S)-N-[3-[[[3-(5-amino-2-pyridyl)-1-[[4-(difluoromethylene)-1-piperidyl]carbonyl]propyl]amino]sulphonyl][1,1'-diphenyl]-2-yl]acetamide hydrochloride is obtained in the form of a white powder.

Yield (%)=60; m.p. (°C.)=184–186;

$[\alpha]_D^{20}$ (°)=+118 (c=0.23; methanol)

Key to the tables which follow:

in the "salt" column, "HCl" corresponds to a hydrochloride and the ratio in parentheses is the (acid:base) ratio, in the "$[\alpha]_D^{20}$" column, c=0.2; methanol except for compounds 9 and 11 (c=0.4; methanol).

TABLE 1
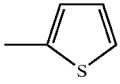
(I₁)
| No. | R₃ | X | A | R₂ | B | Salt | Melting point (° C.) | $[\alpha]_D^{20}$ (°) |
|---|---|---|---|---|---|---|---|---|
| 1 | —COCH₂CH₃ | CH | 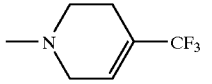 | 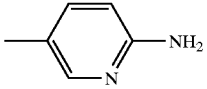 | 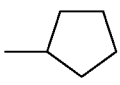 | HCl (1:1) | 155–159 | +89 |
| 2 | —COCH₂CH₃ | CH | 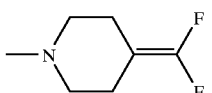 | 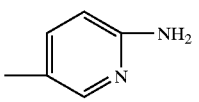 | 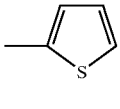 | HCl (1:1) | 128–133 | +86 |
| 3 | —COCH₂CH₃ | CH | 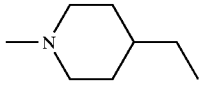 | 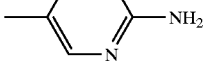 | 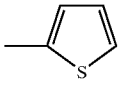 | HCl (1:1) | 144–148 | +120 |
| 4 | —COCH₂CH₃ | CH | 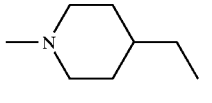 | 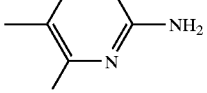 | 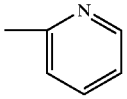 | HCl (1:1) | 145–150 | +110 |
| 5 | —COCH₂CH₃ | CH | 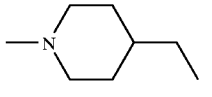 | 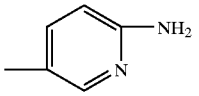 | 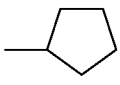 | HCl (2:1) | 145–150 | +138 |
| 6 | —COCH₂CH₃ | CH | 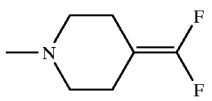 | 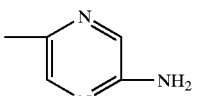 | 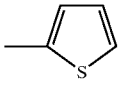 | HCl (1:1) | 136–140 | +103 |
| 7 | —COCH₂CH₃ | CH | 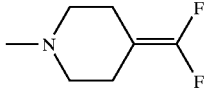 | 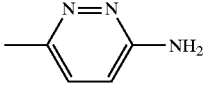 | 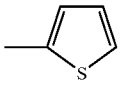 | HCl (1:1) | 140–144 | +60 |
| 8 | —COCH₂CH₃ | CH | 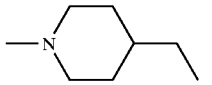 | 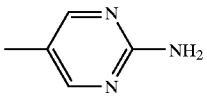 | 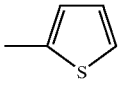 | HCl (1:1) | 122–126 | +83 |
| 9 | —COCH₂CH₃ | CH | 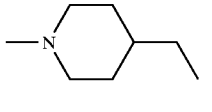 | 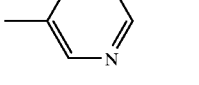 | 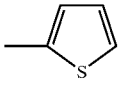 | HCl (1:1) | 112 | +114 |
| 10 | —COCH₂CH₃ | CH | 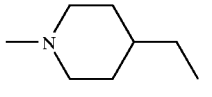 | 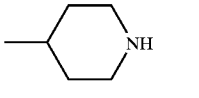 | 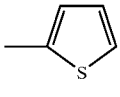 | HCl (1:1) | 134–138 | +112 |
| 11 | —COCH₂CH₃ | CH | 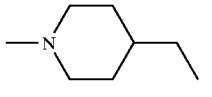 | 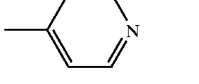 | | HCl (1:1) | 116 | +102 |

TABLE 1-continued (I₁)

| No. | R₃ | X | A | R₂ | B | Salt | Melting point (° C.) | $[\alpha]_D^{20}$ (°) |
|---|---|---|---|---|---|---|---|---|
| 12 | —COCH₂CH₃ | CH | 2-thienyl | N-piperidinyl-4-(=CF₂) | 5-methyl-6-methyl-pyridin-2-yl-amine | HCl (1:1) | 144–148 | +102 |
| 13 | —COCH₂CH₃ | CH | cyclopentyl | N-piperidinyl-4-CF₃ | 5-methyl-pyridin-2-yl-amine | HCl (1:1) | 158–162 | +80 |
| 14 | —COCH₂CH₃ | CH | 2-thienyl | N-piperidinyl-4-(=CF₂) | 5-methyl-pyridin-2-yl-amine | HCl (1:1) | 135–140 | +108 |
| 15 | —COCH₂CH₃ | CH | cyclopentyl | N-piperidinyl-4-ethyl | 5-methyl-pyrazin-2-yl-amine | HCl (1:1) | 142–146 | +103 |
| 16 | —COCH₂CH₃ | CH | 2-thienyl | N-piperidinyl-4-(=CF₂) | 5-methyl-pyrazin-2-yl-amine | — | 154–158 | +123 |
| 17 | —COCH₂CH₃ | CH | 2-thienyl | N-piperidinyl-4-ethyl | 5-methyl-pyrazin-2-yl-amine | HCl (1:1) | 146–150 | +139 |
| 18 | —COCH₂CH₃ | CH | 2-thienyl | N-piperidinyl-4-ethyl | 6-methyl-pyridazin-3-yl-amine | HCl (1:1) | 143–147 | +62 |
| 19 | —COCH₂CH₃ | CH | cyclopentyl | N-piperidinyl-4-ethyl | 5-methyl-pyridin-2-yl-amine | HCl (1:1) | 132–136 | +93 |
| 20 | —COCH₂CH₃ | CH | 2-thienyl | N-piperidinyl-4-ethyl | 6-methyl-pyridin-3-yl-amine | HCl (1:1) | 142–146 | +111 |
| 21 | —COCH₂CH₃ | CH | cyclopentyl | N-piperidinyl-4-(=CF₂) | 5-methyl-6-methyl-pyridin-2-yl-amine | HCl (1:1) | 145–149 | +128 |

TABLE 1-continued
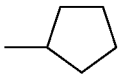
(I₁)
| No. | R₃ | X | A | R₂ | B | Salt | Melting point (° C.) | $[\alpha]_D^{20}$ (°) |
|---|---|---|---|---|---|---|---|---|
| 22 | —COCH₂CH₃ | CH | 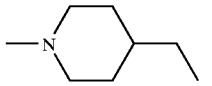 | 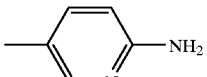 | 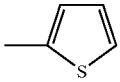 | HCl (1:1) | 140–144 | +97 |
| 23 | —COCH₂CH₃ | CH | 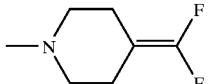 | 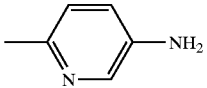 | 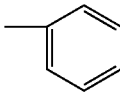 | HCl (1:1) | 152–156 | +82 |
| 24 | —COCH₂CH₃ | CH | 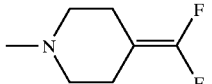 | 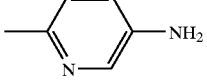 | 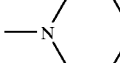 | HCl (1:1) | 136–140 | +90 |
| 25 | —COCH₂CH₃ | CH | 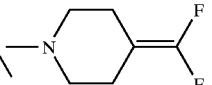 | 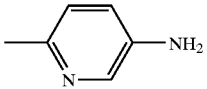 | 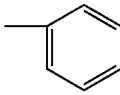 | HCl (1:1) | 146–150 | +76 |
| 26 | —COCH₂CH₃ | CH | 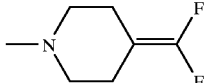 | 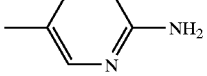 | 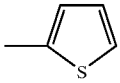 | HCl (1:1) | 146–150 | +101 |
| 27 | —COCH₂CH₃ | CH | 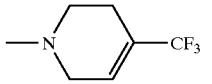 | 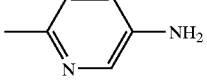 | 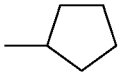 | HCl (1:1) | 142–146 | +65 |
| 28 | —COCH₂CH₃ | CH | 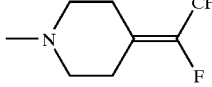 | 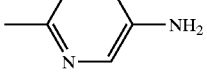 | 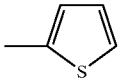 | HCl (1:1) | 150–154 | +66 |
| 29 | —COCH₂CH₃ | CH | 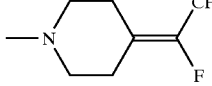 | 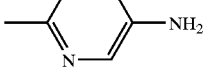 | 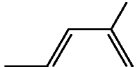 | HCl (1:1) | 160–164 | +69 |
| 30 | —COCH₂CH₃ | CH | 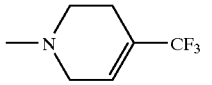 | 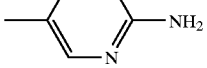 | 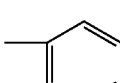 | HCl (1:1) | 150–154 | +72 |
| 31 | —COCH₂CH₃ | CH | 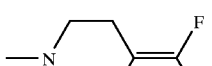 | 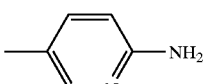 |  | HCl (1:1) | 149–152 | +118 |

TABLE 1-continued
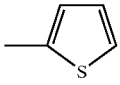
(I₁)
| No. | R₃ | X | A | R₂ | B | Salt | Melting point (° C.) | $[\alpha]_D^{20}$ (°) |
|---|---|---|---|---|---|---|---|---|
| 32 | —COCH₂CH₃ | CH | 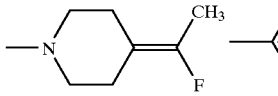 | 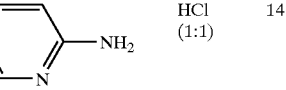 | 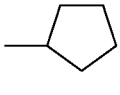 | HCl (1:1) | 146–150 | 155 |
| 33 | —COCH₂CH₃ | CH | 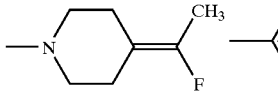 | 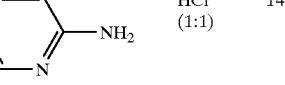 | 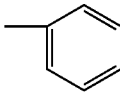 | HCl (1:1) | 143–147 | +56 |
| 34 | —COCH₂CH₃ | CH | 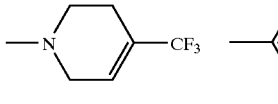 | 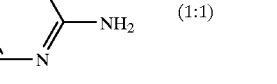 | 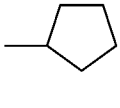 | HCl (1:1) | 144–148 | +95 |
| 35 | —COCH₂CH₃ | CH | 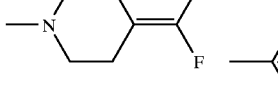 | 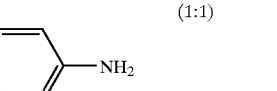 | 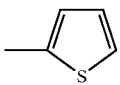 | HCl (1:1) | 146–150 | +77 |
| 36 | —COCH₂CH₃ | CH | 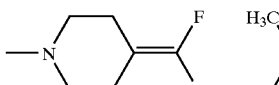 | 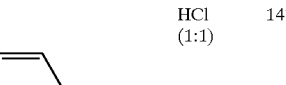 | 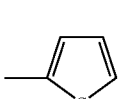 | HCl (1:1) | 147–151 | +122 |
| 37 | —COCH₂CH₃ | CH | 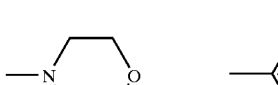 | 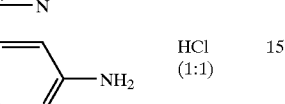 | 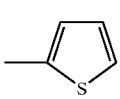 | HCl (1:1) | 159–163 | +114 |
| 38 | —COCH₂CH₃ | CH | 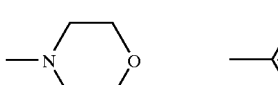 | 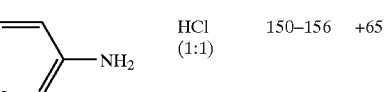 | 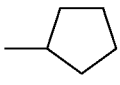 | HCl (1:1) | 150–156 | +65 |
| 39 | —COCH₃ | CH | 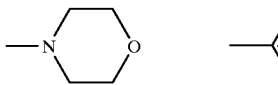 | 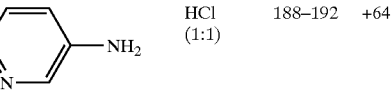 | 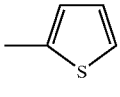 | HCl (1:1) | 188–192 | +64 |
| 40 | —COCH₂CH₃ | CH |  | 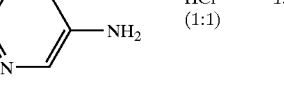 | 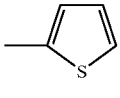 | HCl (1:1) | 153–157 | +74 |
| 41 | —COCH₂CH₃ | CH | 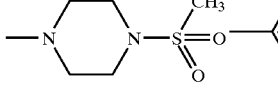 | 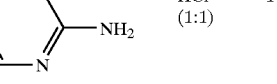 | | HCl (1:1) | 166–170 | +95 |
| 42 | —COCH₂CH₃ | CH | 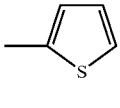 | 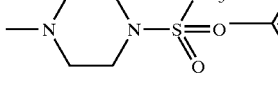 | 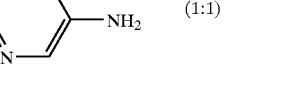 | HCl (1:1) | 172–176 | +62 |

TABLE 1-continued (I₁)

| No. | R₃ | X | A | R₂ | B | Salt | Melting point (° C.) | $[\alpha]_D^{20}$ (°) |
|---|---|---|---|---|---|---|---|---|
| 43 | —COCH₃ | CH | cyclopentyl | 4-(difluoromethylene)piperidin-1-yl | 5-amino-4-ethylpyridin-2-yl | HCl (1:1) | 138–142 | +85 |
| 44 | —COCH₂CH₃ | CH | 2-thienyl | 4-(difluoromethylene)piperidin-1-yl | 5-amino-3-methoxy-6-methylpyridin-2-yl | HCl (1:1) | 157–161 | +102 |
| 45 | —COCH₂CH₃ | CH | 2-thienyl | 4-(difluoromethylene)piperidin-1-yl | 5-amino-3-methyl-6-methylpyridin-2-yl | HCl (1:1) | 156–160 | +86 |
| 46 | —COCH₂CH₃ | CH | cyclopentyl | 4-(difluoromethylene)piperidin-1-yl | 5-aminopyridin-2-yl | HCl (1:1) | 163–167 | +70 |
| 47 | —COCH₃ | CH | 2-thienyl | 4-(difluoromethylene)piperidin-1-yl | 5-amino-6-methylpyridin-2-yl | HCl (1:1) | 152–156 | +92 |
| 48 | —COCH₃ | CH | 3-fluorophenyl | 4-(difluoromethylene)piperidin-1-yl | 5-amino-6-methylpyridin-2-yl | HCl (1:1) | 154–158 | +91 |
| 49 | —COCH₂CH₃ | CH | phenyl | 4-(difluoromethylene)piperidin-1-yl | 5-amino-6-methylpyridin-2-yl | HCl (1:1) | 154–158 | +78 |
| 50 | —COCH₃ | CH | 2-thienyl | 4-methylpiperidin-1-yl | 5-amino-6-methylpyridin-2-yl | HCl (1:1) | 156–160 | +91 |
| 51 | —COCH₃ | CH | cyclopentyl | 4-(difluoromethylene)piperidin-1-yl | 6-amino-3-methylpyridin-... | HCl (1:1) | 148–152 | +79 |

TABLE 1-continued
(I₁)
| No. | R₃ | X | A | R₂ | B | Salt | Melting point (°C.) | $[\alpha]_D^{20}$ (°) |
|---|---|---|---|---|---|---|---|---|
| 52 | —COCH₃ | CH | 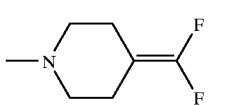 | 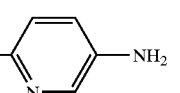 | 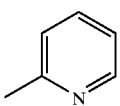 | HCl (1:1) | 170–174 | +90 |
| 53 | —COCH₂CH₃ | CF | 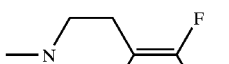 | 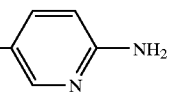 | 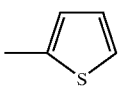 | HCl (1:1) | 150–154 | +88 |
| 54 | —COCH₃ | CH | 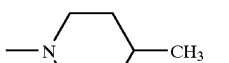 | 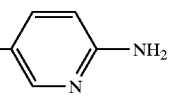 | 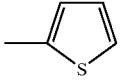 | HCl (1:1) | 170–172 | +132 |
| 55 | —COCH₃ | CH | 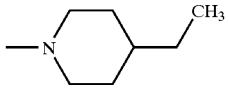 | 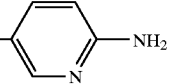 | 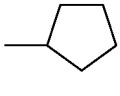 | HCl (1:1) | 166–168 | +122 |
| 56 | —COCH₃ | CH | 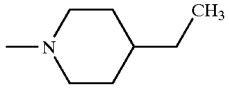 | 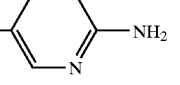 | 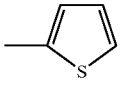 | HCl (1:1) | 160–162 | +82 |
| 57 | —COCH₂CH₃ | CF | 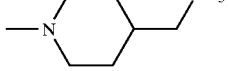 | 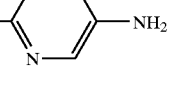 | 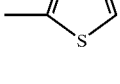 | HCl (1:1) | 150–154 | +39 |
| 58 | —COCH₂CH₃ | CF | 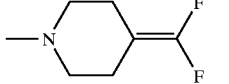 | 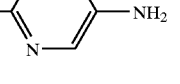 | 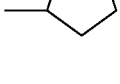 | HCl (1:1) | 148–152 | +90 |
| 59 | —COCH₃ | CH | 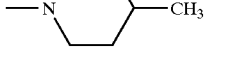 | 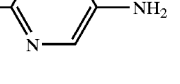 | 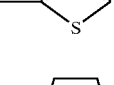 | HCl (1:1) | 148–152 | +77 |
| 60 | —COCH₂CH₃ | CH | 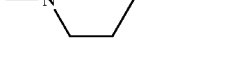 | 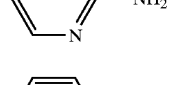 |  | HCl (1:1) | 154–158 | +106 |
| 61 | —COCH₂CH₃ | CH | 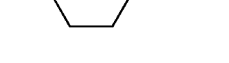 | 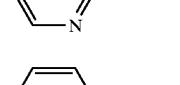 |  | HCl (1:1) | 144–148 | +91 |
| 62 | —COCH₂CH₃ | CH | 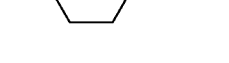 | 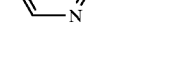 | 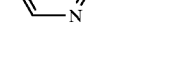 | HCl (1:1) | 158 | +78 |

TABLE 1-continued

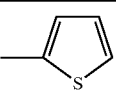

(I₁)

| No. | R₃ | X | A | R₂ | B | Salt | Melting point (° C.) | [α]$_D^{20}$ (°) |
|---|---|---|---|---|---|---|---|---|
| 63 | —COCH₃ | CH | 2-thienyl | N-piperidinyl-4-CH₂OH | 5-amino-2-pyridyl | HCl (1:1) | 162 | +110 |
| 64 | —COCH₂CH₃ | CH | cyclopentyl | N-piperidinyl-4-CH₂F | 5-amino-2-pyridyl | HCl (1:1) | 148 | +86 |
| 65 | —COCH₃ | CH | cyclopentyl | N-piperidinyl-4-C₂H₅ | 5-amino-2-pyridyl | HCl (1:1) | 148–152 | +81 |
| 66 | —COCH₂CH₃ | CH | cyclopentyl | N-piperidinyl-4-C₂H₅ | 5-amino-2-pyridyl | HCl (1:1) | 146–150 | +67 |
| 67 | —COCH₂CH₂CH₃ | CH | 2-thienyl | N-piperidinyl-4-=CF₂ | 5-amino-2-pyridyl | HCl (1:1) | 140–144 | +102 |
| 68 | —COCH₃ | CH | cyclopentyl | N-piperidinyl-4-=CF₂ | 5-amino-2-pyridyl | HCl (1:1) | 150–154 | +59 |
| 69 | —COCH₂CH₃ | CH | phenyl | N-piperidinyl-4-=CF₂ | 5-(NHCH₃)-2-pyridyl | HCl (1:1) | 154–155 | +85 |
| 70 | —COCH₂CH₃ | CH | phenyl | N-piperidinyl-4-=CF₂ | 5-(NHCH₃)-2-pyridyl | HCl | 139–140 | +100 |
| 71 | —COCH₃ | CH | phenyl | N-piperidinyl-4-CH₃ | 5-amino-2-pyridyl | HCl | 176–180 | +84 |
| 72 | —COCH₂CH₃ | CH | phenyl | N-piperidinyl-4-CH₃ | 5-amino-2-pyridyl | HCl | 178–182 | +71 |
| 73 | —COCH₂CH₃ | CH | 3-methoxyphenyl | N-piperidinyl-4-CH₃ | 5-amino-2-pyridyl | HCl | 138–139 | +155 |

TABLE 1-continued
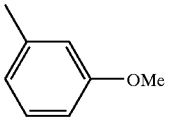
(I₁)
| No. | R₃ | X | A | R₂ | B | Salt | Melting point (° C.) | $[\alpha]_D^{20}$ (°) |
|---|---|---|---|---|---|---|---|---|
| 74 | —COCH₃ | CH | 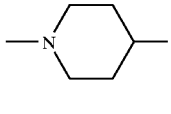 | 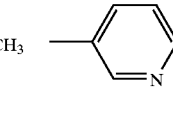 | 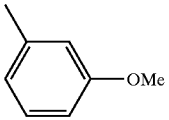 | HCl | 145–146 | +116 |
| 75 | —COCH₂CH₃ | CH | 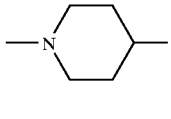 | 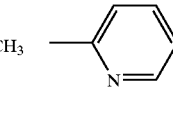 | 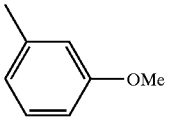 | HCl | 146–147 | +62 |
| 76 | —COCH₃ | CH | 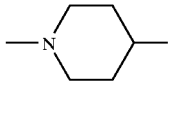 | 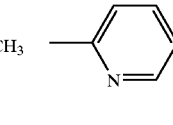 | 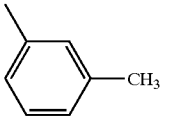 | HCl | 156–157 | +84 |
| 77 | —COCH₃ | CH | 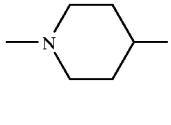 | 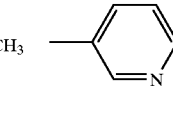 | 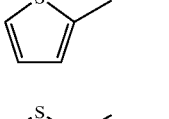 | HCl | 147–148 | +136 |
| 78 | —COCH₃ | CH | 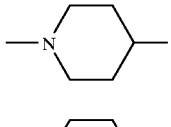 | 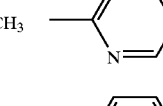 | 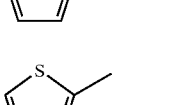 | HCl | 168 | +83 |
| 79 | —COCH₃ | CH | 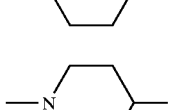 | 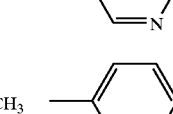 | 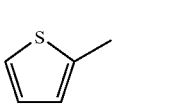 | HCl | 164 | +63 |
| 80 | —COCH₂CH₃ | CH | 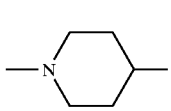 | 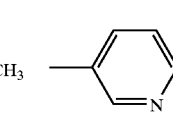 | 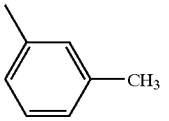 | HCl | 152 | +112 |
| 81 | —COCH₂CH₃ | CH | 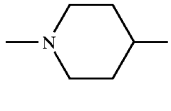 | 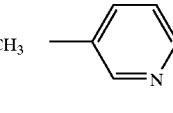 | 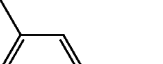 | HCl | 160 | +107 |
| 82 | —COCH₂CH₃ | CH | 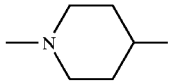 | 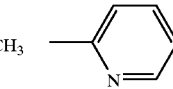 |  | HCl | 155–157 | +130 |
| 83 | —COCH₃ | CH |  |  | | HCl | 159–161 | +106 |

TABLE 1-continued (I₁)

| No. | R₃ | X | A | R₂ | B | Salt | Melting point (° C.) | $[\alpha]_D^{20}$ (°) |
|---|---|---|---|---|---|---|---|---|
| 84 | —COCH₂CH₃ | CH | 2-thienyl | 4-(difluoromethylene)-1-piperidinyl | 5-amino-3-pyridyl | HCl | 160–164 | +105 |
| 85 | —COCH₂CH₃ | CH | phenyl | 4-(difluoromethylene)-1-piperidinyl | 6-amino-3-pyridyl | HCl | 180–184 | +88 |
| 86 | —COCH₂CH₃ | CH | phenyl | 4-(difluoromethylene)-1-piperidinyl | 2-amino-4-pyridyl | HCl | 230–234 | +100 |
| 87 | —COCH₂CH₃ | CH | 2-thienyl | 1-azepanyl | 6-amino-3-pyridyl | HCl | 153–157 | +74 |
| 88 | —COCH₂CH₃ | CH | phenyl | N-methoxy-N-propylamino | 6-amino-3-pyridyl | HCl | 144–148 | +77 |
| 89 | —COCH₂CH₃ | CH | phenyl | N,N-diethylamino | 6-amino-5-methyl-3-pyridyl | HCl | 160–164 | +66 |
| 90 | —COCH₂CH₃ | CH | phenyl | N-methoxy-N-propylamino | 6-amino-4-methyl-3-pyridyl (5-methyl) | HCl | 150–154 | +87 |
| 91 | —COCH₂CH₃ | CBr | phenyl | N,N-dimethylamino | 5-methyl-6-amino-3-pyridyl | HCl | 166–170 | +76 |

TABLE 1-continued
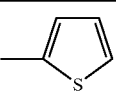
(I₁)
| No. | R₃ | X | A | R₂ | B | Salt | Melting point (° C.) | $[\alpha]_D^{20}$ (°) |
|---|---|---|---|---|---|---|---|---|
| 92 | —COCH₂CH₃ | CH | 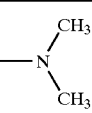 | 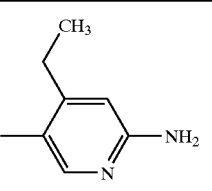 | 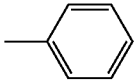 | HCl | 160–164 | +100 |
| 93 | —COCH₂CH₃ | CH | 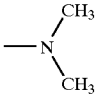 | 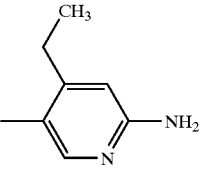 | 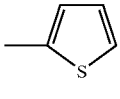 | HCl | 152–156 | +82 |
| 94 | —COCH₃ | CH | 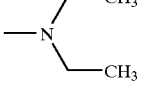 | 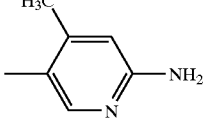 | 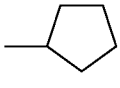 | HCl | 162–166 | +101 |
| 95 | —COCH₃ | CH | 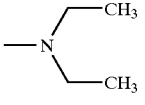 | 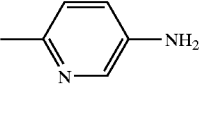 | 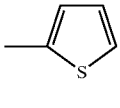 | HCl | 148–152 | +57 |
| 96 | —COCH₃ | CH | 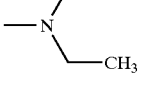 | 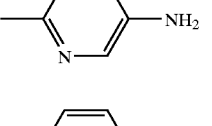 | 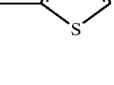 | HCl | 145–149 | +64 |
| 97 | —COCH₃ | CBr | 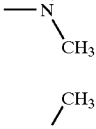 | 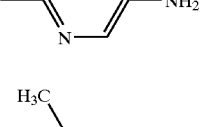 | 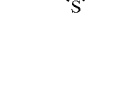 | HCl | 168–172 | +50 |
| 98 | —COCH₃ | CH | 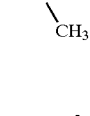 | 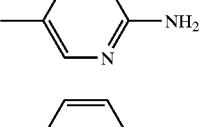 | 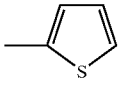 | HCl | 153–158 | +191 |
| 99 | —COCH₂CH₃ | CH | 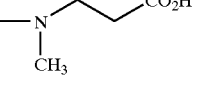 | 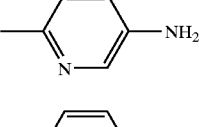 | 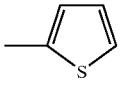 | HCl | 72–76 | +50 |
| 100 | —COCH₂CH₃ | CH | 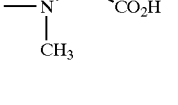 | 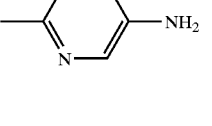 | 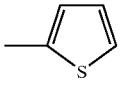 | HCl | 145–149 | +47 |

TABLE 1-continued
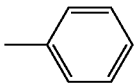
(I₁)
| No. | R₃ | X | A | R₂ | B | Salt | Melting point (° C.) | [α]_D^{20} (°) |
|---|---|---|---|---|---|---|---|---|
| 101 | —COCH₂CH₃ | CH | 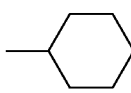 | 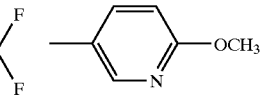 | 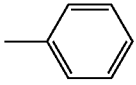 | — | 139 | +127 |
| 102 | —COCH₂CH₃ | CH | 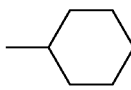 | 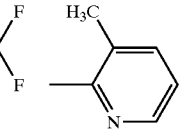 | 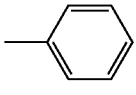 | HCl | 134 | +114 |
| 103 | —COCH₂CH₃ | CH | 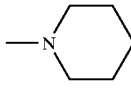 | 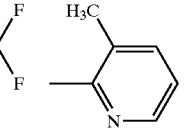 | 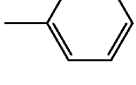 | HCl | 137 | +122 |
| 104 | —COCH₂CH₃ | CH | 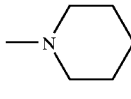 | 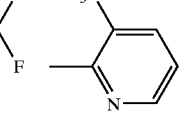 | 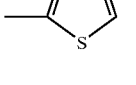 | — | 139 | +132 |
| 105 | —COCH₂CH₃ | CH | 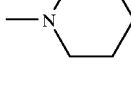 | 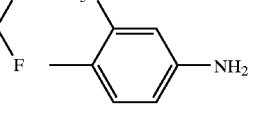 | 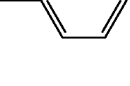 | HCl | 173–177 | +108 |
| 106 | —COCH₂CH₃ | CH | 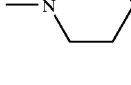 | 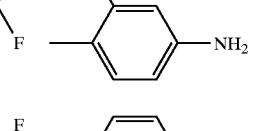 | 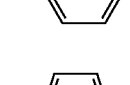 | HCl | 170–174 | +129 |
| 107 | —COCH₂CH₃ | CH | 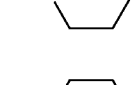 | 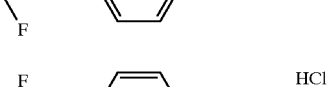 | 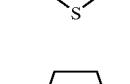 | HCl | 160–164 | +124 |
| 108 | —COCH₂CH₃ | CH | 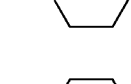 | 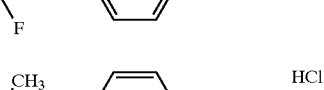 | 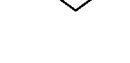 | HCl | 162–164 | +120 |
| 109 | —COCH₂CH₃ | CH | 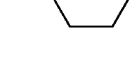 | 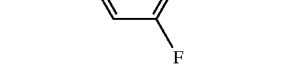 | | HCl | 142–146 | +87 |

TABLE 1-continued

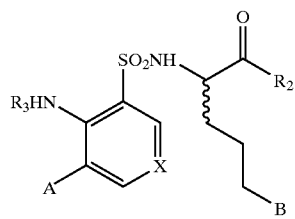

(I₁)

| No. | R₃ | X | A | R₂ | B | Salt | Melting point (° C.) | $[\alpha]_D^{20}$ (°) |
|---|---|---|---|---|---|---|---|---|
| 110 | —COCH₂CH₃ | CH | phenyl | 4-(difluoromethylene)piperidin-1-yl | 3-methyl-4-(NHCH₃)phenyl | HCl | 162–166 | +116 |
| 111 | —COCH₂CH₃ | CH | phenyl | 4-(difluoromethylene)piperidin-1-yl | 4-methoxy-3-methyl-6-aminopyridin-5-yl | HCl | 165–169 | +94.5 |
| 112 | —COCH₂CH₃ | CH | phenyl | 4-(difluoromethylene)piperidin-1-yl | 5-chloro-2-methyl-6-aminopyridin-3-yl | HCl | 156–160 | +83 |
| 113 | —COCH₂CH₃ | CH | phenyl | 4-(difluoromethylene)piperidin-1-yl | 4-chloro-6-amino-pyridin-3-yl | HCl | 158–162 | +109 |
| 114 | —COCH₂CH₃ | N | phenyl | 4-methylpiperidin-1-yl | 5-amino-pyridin-2-yl | HCl | 180–184 | +100 |
| 115 | —COCH₂CH₃ | N | phenyl | 4-methylpiperidin-1-yl | 6-amino-pyridin-3-yl | HCl | 178–182 | +85 |
| 116 | —COCH₂CH₃ | N | 2-thienyl | 4-methylpiperidin-1-yl | 6-amino-pyridin-3-yl | HCl (2:1) | 190–194 | +73 |
| 117 | —COCH₂CH₃ | N | 2-thienyl | 4-methylpiperidin-1-yl | 6-amino-pyridin-3-yl | HCl (1.5:1) | 180–184 | +91 |
| 118 | —CHO | CH | 3-methylphenyl | 4-(difluoromethylene)piperidin-1-yl | 6-amino-pyridin-3-yl | HCl | 168 | +108 |

TABLE 2
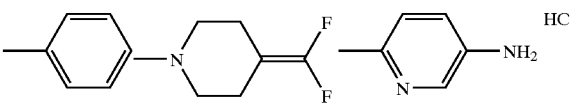
(I₂)
| No. | R₃ | X | A | R₂ | B | Salt | Melting point (° C.) | [α]_D^{20} (°) |
|---|---|---|---|---|---|---|---|---|
| 119 | —COCH₃ | CH | 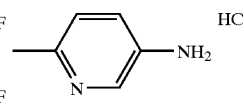 | 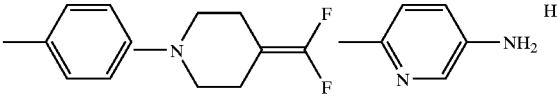 | 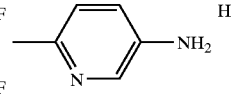 | HCl | 166 | +52 |
TABLE 3
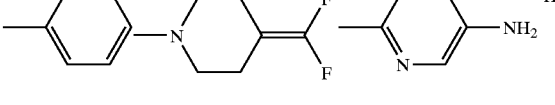
(I₃)
with R₃ = —COCH₃ and X = CH
| No. | Configuration of the double bond | A | R₂ | B | Salt | Melting point (° C.) | [α]_D^{20} (°) |
|---|---|---|---|---|---|---|---|
| 120 | cis | 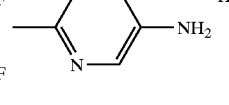 | 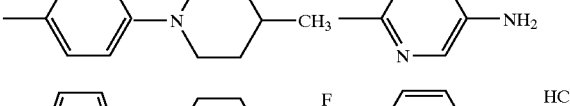 | 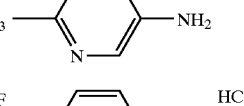 | HCl | 161 | +68 |
| 121 | trans | 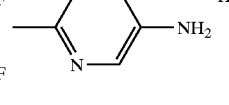 | 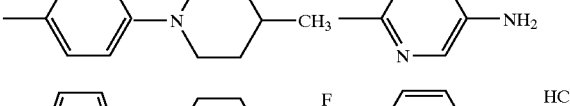 | 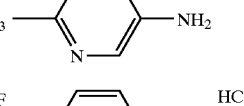 | HCl | 175 | +76 |
| 122 | cis | 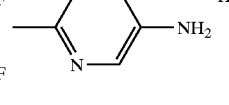 | 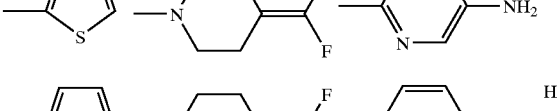 | 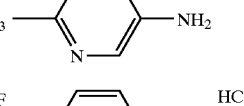 | HCl | 119 | +134 |
| 123 | cis | 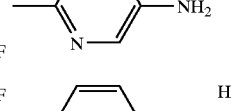 | 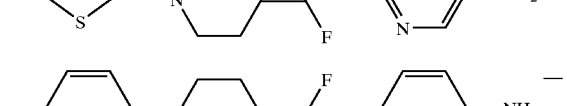 | 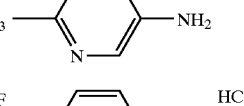 | HCl | 170 | +40 |
| 124 | trans | 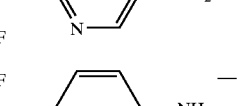 | 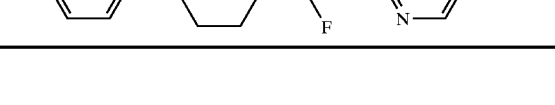 | 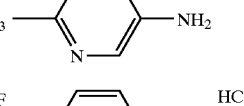 | HCl | 173.5 | +87 |
| 125 | trans | 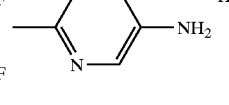 | 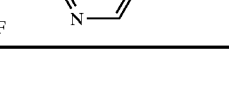 | 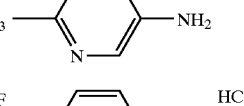 | — | — | — |

TABLE 4

(I₄)

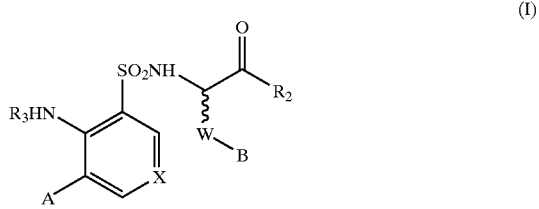

| No. | R₃ | X | A | R₂ | B | Salt | Melting point (° C.) | $[\alpha]_D^{20}$ (°) |
|---|---|---|---|---|---|---|---|---|
| 126 | —COCH₃ | CH | | | | HCl | 184–6 | +118 (c = 0.23) |

The compounds of the invention underwent pharmacological studies which demonstrated their antithrombotic and anticoagulant properties, and their value as therapeutically active substances.

1. Determination of the Inhibition Constants (Ki) with Respect to Thrombin (In vitro)

25 μl of a solution of test compound (7 concentrations are studied), 50 μl of a solution of chromogenic substrate (2 concentrations are studied; S2238 Chromogenix™) dissolved in Tris buffer at pH 7.5 (50 mM Tris, 100 mM NaCl and 0.1% BSA) and finally 25 μl of a 0.24 U/ml thrombin solution are placed in each well of a 96-well microplate. The release of 4-nitroaniline is monitored at 405 nm using a plate reader.

The $K_i$ is determined by the Dixon method.

The compounds of the invention inhibit human thrombin and their $K_i$ is between 0.001 and 100 μM.

2. Anticoagulant Activity on Rat Plasma (Ex vivo)

Male CD rats weighing 200 to 250 g are treated with the test compound or with its vehicle orally. The animals are then anaesthetized with Nembutal™ (60 mg/kg; 0.1 ml/kg), blood is collected over 3.8% trisodium citrate (1 vol/9 vol of blood) from the retro-orbital sinus and the plasma is prepared by centrifugation at 3000×g for 15 minutes at room temperature. 200 μl of plasma are then incubated at 37° C. with 200 μl of thrombin solution, the final thrombin concentration being 0.75 NIH units/ml, and the clotting time is noted.

The anticoagulant effect is expressed as a percentage increase in the thrombin time on the plasmas collected 30 and 90 minutes after administering 20 mg/kg p.o.; it is between 100 and 2000%.

3. Antithrombotic Activity in Rats in a Model of Mixed Arterio-venous Thrombosis (In vivo)

The formation of a thrombus in rats is obtained by placing a shunt between the left jugular vein and the right carotid artery; cotton thread impregnated with thromboplastin (Tissue Factor or TF) is inserted into the shunt. The compound is administered orally in several doses 30 or 60 minutes before installing the shunt. Five minutes after installing the shunt, the thrombus formed on contact with the thread +TF is removed and rapidly weighed. The antithrombotic activity is evaluated by the reduction in the fresh weight of the thrombus (mg) in the animals treated with the compound, compared with the control animals treated with its vehicle.

The antithrombotic activity is expressed as an $AD_{50}$, the dose which reduces the weight of the fresh thrombus by 50% dependent. This dose is between 0.1 and 50 mg/kg.

4. Membrane Permeability In vitro

The compounds of the invention are evaluated in a model of membrane permeability on a Caco-2 cell line obtained from a human adenocarcinoma. This cell line constitutes a model of choice for studying the absorption of xenobiotics [P. Artusson, Therapeutics Drug Carrier System (1991), 8(4), pp 305–330]. The passage of the compounds of the invention is expressed as a function of the amount of product which has crossed the cell barrier in 2 h. The values are between 0 and 50%.

The compounds of the invention may be useful in any clinical indication associated with thrombosis or in an indication in which thrombotic complications may occur.

To this end, they may be provided in any form which is suitable for oral, parenteral or intravenous administration, such as plain tablets, coated tablets, gel capsules, wafer capsules, drinkable or injectable suspensions or solutions, etc., in combination with suitable excipients. All these forms are dosed to allow an administration of from 1 to 1000 mg per day and per patient, in one or more doses.

What is claimed is:

1. A compound of formula (I):

(I)

wherein:
X is a nitrogen atom or CR₄ in which R₄ is hydrogen or halogen;
W is —(CH₂)₂—, —(CH₂)₃—, —CH₂—C≡C— or —CH₂—CH=CH—,
R₂ is:
  piperidyl optionally substituted:
    with one or two groups chosen from hydroxyl, (C₁–C₄)alkyl, hydroxy(C₁–C₄)alkyl, C₁–C₄) alkoxy(C₁–C₄)alkyl, (C₁–C₄)alkoxy, (C₁–C₄) alkylthio, monofluoromethyl, difluoromethyl, trifluoromethyl and (C₃–C₆)cycloalkyl,
    with a group =CYZ in which Y and Z are independently hydrogen, halogen or (C₁–C₄)alkyl optionally substituted with 1 to 3 halogen atoms, with a group

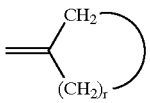

in which r is 1 to 3, or
with a spiro $(C_3–C_6)$cycloalkane group;
1,2,3,6-tetrahydropyridyl optionally substituted with a $(C_1–C_4)$alkyl group, said $(C_1–C_4)$alkyl group being optionally substituted with 1 to 3 halogen atoms or a $(C_3–C_6)$cycloalkyl group;
hexahydro-1H-azepinyl optionally substituted in position 4 with a trifluoromethyl or difluoromethylene group;
heptahydroazocin-1-yl;
octahydro-1H-azonin-1-yl;
a group

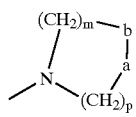

in which a-b is —CONR'—, m=1 to 2, p=1 to 2 and R' is hydrogen or $(C_1–C_4)$alkyl;
a group

in which $R_{12}$ is $(C_1–C_4)$alkyl, carboxy$(C_1–C_4)$alkyl or $(C_1–C_4)$alkoxycarbonyl$(C_1–C_4)$alkyl and $R_{13}$ is $(C_1–C_4)$alkoxy or $(C_1–C_4)$alkyl, or $R_{12}$ is $(C_1–C_4)$alkyl or $CH_2CF_3$ and $R_{13}$ is a group

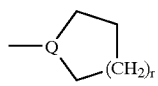

in which Q is a carbon or nitrogen atom and r is 1 to 3;
piperazinyl optionally substituted with $(C_1–C_4)$alkyl or $(C_1–C_4)$alkylsulphonyl; or morpholinyl;
$R_3$ is:
$(C_1–C_5)$alkyl; or
—$COR_1$, in which $R_1$ is hydrogen, $(C_1–C_4)$alkyl, —$(CH_2)_nOCH_3$, —$CH_2O(C_2H_4O)_nCH_3$, —$(CH_2)_nCF_3$ or —$(CH_2)_nOH$ and n is 1 to 4;
—$SO_2R_5$;
—$CONHR_5$; or
—$SO_2N(R_5)_2$, $R_5$ is $(C_1–C_4)$alkyl;
A is:
$(C_5–C_8)$cycloalkyl; or
phenyl, pyridyl, thienyl, furyl, pyrimidinyl or thiazolyl, said groups optionally substituted with 1 to 3 substituents chosen from halogen, $(C_1–C_4)$alkyl, $(C_1–C_4)$alkoxy, trifluoromethyl, trifluoromethoxy, —$CH_2OR_{10}$, —$CH_2OCOR_{10}$, —$CH_2OCONR_{10}R_{11}$, —$COOR_{10}$, —$CONR_{10}R_{11}$, nitro, —$NR_{10}R_{11}$, —$NHCOR_{10}$ and —$NH(CH_2)_qOR_{10}$, in which $R_{10}$ and $R_{11}$ are independently hydrogen or $(C_1–C_4)$alkyl and q is from 0 to 6; and B is:
pyridyl optionally substituted with 1 or 2 substituents chosen from $(C_1–C_4)$alkyl, hydroxyl and $(C_1–C_4)$alkoxy;
aminopyrazinyl;
aminopyridazinyl;
pyrimidinyl optionally substituted with an amino group;
piperidyl;
aminopyridyl optionally substituted on the pyridine with $(C_1–C_4)$alkyl, $(C_1–C_4)$alkoxy or halogen and optionally substituted on the amino group with $(C_1–C_4)$alkyl;
aminophenyl optionally substituted on the amino group with $(C_1–C_4)$alkyl and on the phenyl group with $(C_1–C_4)$alkyl or halogen; or
a pharmaceutically acceptable acid-addition salt thereof.

2. A compound according to claim 1, wherein
$R_2$ is:
piperidyl optionally substituted with one or two groups chosen from hydroxyl, $(C_1–C_4)$alkyl, hydroxy$(C_1–C_4)$alkyl, $(C_1–C_4)$alkoxy$(C_1–C_4)$alkyl, $(C_1–C_4)$alkoxy, $(C_1–C_4)$alkylthio, monofluoromethyl, difluoromethyl, trifluoromethyl and $(C_3–C_6)$cycloalkyl, or with a group =CYZ in which Y and Z are independently hydrogen, halogen or $(C_1–C_4)$alkyl optionally substituted with 1 to 3 halogen atoms;
1,2,3,6-tetrahydropyridyl optionally substituted with a $(C_1–C_4)$alkyl group, said $(C_1–C_4)$alkyl group being optionally substituted with 1 to 3 halogen atoms or a $(C_3–C_6)$cycloalkyl group;
hexahydro-1H-azepinyl optionally substituted in position 4 with a trifluoromethyl or difluoromethylene group;
a group

in which $R_{12}$ is $(C_1–C_4)$alkyl, carboxy$(C_1–C_4)$alkyl or $(C_1–C_4)$alkoxycarbonyl$(C_1–C_4)$alkyl and $R_{13}$ is $(C_1–C_4)$alkoxy or $(C_1–C_4)$alkyl;
piperazinyl optionally substituted with $(C_1–C_4)$alkyl or $(C_1–C_4)$alkylsulphonyl; or morpholinyl; and
$R_3$ is:
$(C_1–C_5)$alkyl; or
—$COR_1$, in which $R_1$ is hydrogen, $(C_1–C_4)$alkyl, —$(CH_2)_nOCH_3$, —$CH_2O(C_2H_4O)_nCH_3$, —$(CH_2)_nCF_3$ or —$(CH_2)_nOH$ and n is 1 to 4.

3. A compound according to claim 1 wherein
W is —$(CH_2)_3$— or —$CH_2$—CH=CH—;
$R_2$ is:
piperidyl optionally substituted with one or two groups chosen from hydroxyl, $(C_1–C_4)$alkyl, hydroxy$(C_1–C_4)$alkyl, $(C_1–C_4)$alkoxy$(C_1–C_4)$alkyl, $(C_1–C_4)$alkylthio, monofluoromethyl, difluoromethyl and trifluoromethyl, or with a group =CYZ in which Y and Z are independently hydrogen, halogen or $(C_1–C_4)$alkyl optionally substituted with 1 to 3 halogen atoms;

1,2,3,6-tetrahydropyridyl optionally substituted with ($C_1$–$C_4$)alkyl said ($C_1$–$C_4$)alkyl group being optionally substituted with 1 to 3 halogen atoms;
hexahydro-1H-azepinyl;
piperazinyl optionally substituted with ($C_1$–$C_4$) alkylsulphonyl; or
morpholinyl;
$R_3$ is —$COR_1$, in which $R_1$ is ($C_1$–$C_4$)alkyl, —$(CH_2)_n$ $OCH_3$ or —$(CH_2)_nCF_3$ and n is 1 to 4; and
A is:
phenyl optionally substituted with 1 to 3 substituents chosen from halogen, —($C_1$–$C_4$)alkyl and ($C_1$–$C_4$) alkoxy;
a heterocycle chosen from pyridyl and thienyl groups; or
($C_5$–$C_8$)cycloalkyl.

4. A compound according to claim 2 wherein
W is —$(CH_2)_3$— or —$CH_2$—CH=CH—;
$R_2$ is:
piperidyl optionally substituted with one or two groups chosen from hydroxyl, ($C_1$–$C_4$)alkyl, hydroxy($C_1$–$C_4$)alkyl, ($C_1$–$C_4$)alkoxy($C_1$–$C_4$)alkyl, ($C_1$–$C_4$) alkoxy, ($C_1$–$C_4$)alkylthio, monofluoromethyl, difluoromethyl and trifluoromethyl, or with a group =CYZ in which Y and Z are independently hydrogen, halogen or ($C_1$–$C_4$)alkyl optionally substituted with 1 to 3 halogen atoms;
1,2,3,6-tetrahydropyridyl optionally substituted with ($C_1$–$C_4$)alkyl said ($C_1$–$C_4$)alkyl group being optionally substituted with 1 to 3 halogen atoms;
hexahydro-1H-azepinyl;
piperazinyl optionally substituted with ($C_1$–$C_4$) alkylsulphonyl; or
morpholinyl;
$R_3$ is —$COR_1$, in which $R_1$ is ($C_1$–$C_4$)alkyl, —$(CH_2)_n$ $OCH_3$ or —$(CH_2)_nCF_3$ and n is 1 to 4; and
A is:
phenyl optionally substituted with 1 to 3 substituents chosen from halogen, —($C_1$–$C_4$)alkyl and ($C_1$–$C_4$) alkoxy;
a heterocycle chosen from pyridyl and thienyl groups; or
($C_5$–$C_8$)cycloalkyl.

5. A compound selected from the group consisting of:

—N-[2-[[[(1S)-4-(5-amino-3-methylpyrid-2-yl)-1-[[4-(difluoromethylene)piperid-1-yl]carbonyl]butyl]amino] sulphonyl]-6-thien-2-ylphenyl]propanamide,
—N-[2-[[[(1S)-4-(6-amino-4-ethylpyrid-3-yl)-1-[[4-(difluoromethylene)piperid-1-yl]carbonyl]butyl]amino] sulphonyl]-6cyclopentylphenyl]acetamide,
N-[3-[[[(1S)-4(5-aminopyrid-2-yl)-1-[[4-(difluoromethylene)piperid-1-yl]carbonyl]butyl]amino] sulphonyl]-3'-fluoro[1,1'-diphenyl]-2-yl]propanamide,
N-[3-[[[(1S)-4-(5-aminopyrid-2-yl)-1-[[4-(difluoromethylene)piperid-1-yl]carbonyl]butyl]amino] sulphonyl]-3'-fluoro[1,1'-diphenyl]-2-yl]acetamide,
N-[2-[[[(1S)-4-(5-aminopyrid-2-yl)-1-[(4-ethylpiperid-1-yl)carbonyl]butyl]amino]sulphonyl]-6-thien-2-ylphenyl] propanamide,
N-[2-[[[(1S)-4-(6-aminopyrid-3-yl)-1-piperid-1-ylcarbonyl)butyl]amino]sulphonyl]-6-cyclopentylphenyl] propanamide,
N-[2-[[[(1S)-4-(5-aminopyrid-2-yl)-1-[[4-(difluoromethylene)piperid-1-yl]carbonyl]butyl]amino] sulphonyl]-6-cyclopentylphenyl]propanamide,
N-[3-[[[(1S)-4-(5-aminopyrid-2-yl)-1-[[4-(difluoromethylene)piperid-1-yl]carbonyl]butyl]amino] sulphonyl][1,1'-diphenyl]-2-yl]acetamide,
N-[2-[[[(1S)-4-(6-aminopyrid-3-yl)-1-[[4-(difluoromethylene)piperid-1-yl]carbonyl]butyl]amino] sulphonyl]-6-thien-2-ylphenyl]acetamide,
N-[2-[[[(1S)-4-(6-amino-4-methylpyrid-3-yl)-1-[[4-(difluoromethylene)piperid-1-yl]carbonyl]butyl]amino] sulphonyl]-6-thien-2-ylphenyl]propanamide,
N-[2-[[[(1S)-4-(6-aminopyrid-3-yl)-1-[[4-(difluoromethylene)piperid-1-yl]carbonyl]butyl]amino] sulphonyl]-6-cyclopentylphenyl]acetamide,
N-[2-[[[(1S)-4(aminopyrid-3-yl)-1-[[4-(trifluoromethyl)-1,2,3,6-tetrahydropyrid-1-yl]carbonyl]butyl]amino] sulphonyl]-6-thien-2-ylphenyl]propanamide,
N-[2-[[[(1S)-4-(6-aminopyrid-3-yl)-1-[[4-(difluoromethylene)piperid-1-yl]carbonyl]butyl]amino] sulphonyl]-6-cyclopentylphenyl]propanamide,
N-[3-[[[(1S)-4-(5-aminopyrid-2-yl)-1-[[4 (difluoromethylene)piperid-1-yl]carbonyl]butyl]amino] sulphonyl][1,1'-diphenyl]-2-yl]propanamide,
N-[2-[[[(1S)-4-(6amino-4-methylpyrid-3-yl)-1-[[4-difluoromethylene)piperid-1-yl]carbonyl]butyl]amino] sulphonyl]-6-cyclopentylphenyl]propanamide,
N-[3-[[[(1S)-4-(6-aminopyrid-3-yl)-1-[[4-(difluoromethylene)piperid-1-yl]carbonyl]butyl]amino] sulphonyl]-3'-fluoro[1,1'-diphenyl]-2-yl]propanamide,
N-[2-[[[(1S)-4-(5-aminopyrid-2-yl)-1-[(4methylpiperid-1-yl)carbonyl]butyl]amino]sulphonyl]-6-thien-2-ylphenyl] acetamide,
N-[2-[[[(1S)-4-(6-aminopyrid-3-yl)-1-[(4-ethylpiperid-1-yl)carbonyl]butyl]amino]sulphonyl]-6-thien-2-ylphenyl] propanamide,
N-[2-[[[(1S)-4-(6-aminopyrid-3-yl)-1-[(4-methylpiperid-1-yl)carbonyl]butyl]amino]sulphonyl]-6-cyclopentylphenyl]acetamide,
N-[3-[[[(1S)-4-(5-aminopyrid-2-yl)-1-[(4-methylpiperid-1-yl)carbonyl]butyl]amino]sulphonyl]-3'-methyl[1,1'-diphenyl]-2-yl]acetamide,
N-[3-[[[(1S)-4-(6amino-4-methoxypyrid-3-yl-1-[[4-(difluoromethylene)piperid-1-yl]carbonyl]butyl]amino] sulphonyl][1,1'-diphenyl]-2-yl]propanamide,
N-[3-[[[(1S)-4-(5-aminopyrid-2-yl)-1[(4-methylpiperid-1-yl)carbonyl]butyl]amino]sulphonyl]-3'-methyl[1,1'-diphenyl]-2-yl]propanamide,
N-[3-[[[(1S)-4-(5-aminopyrid-2-yl)-1-[(4-methylpiperid-1-yl)carbonyl]butyl]amino]sulphonyl]-3'-fluoro[1,1'-diphenyl]-2-yl]acetamide,
N-[3-[[[(1S)-4-(5-aminopyrid-2-yl)-1-[(4-methylpiperid-1-yl)carbonyl]butyl]amino]sulphonyl]-3'-methoxy[1,1'-diphenyl]-2-yl]propanamide,
N-[(1S)-4-(5-amino-2-pyridyl)-1-[[4-(difluoromethylene)-1-piperidyl]carbonyl]butyl]-2-(formylamino)-3'-methyl [1,1'-diphenyl]-3-sulphonamide,
N-[3-[[[(1S,3Z)-4-(5-amino-2-pyridyl)-1-[[4-(difluoromethylene)-1-piperidyl]carbonyl]-3-butenyl] amino]sulphonyl][1,1'-diphenyl]-2-yl]acetamide, and
N-[3-[[[(1S,3Z)-4-(5-amino-2-pyridyl)-1-[(4-methyl-1-piperidyl)carbonyl]-3-butenyl]amino]sulphonyl][1,1'-diphenyl]-2-yl]acetamide, or
a pharmaceutically acceptable acid-addition salt thereof.

6. A compound according to claim 1 wherein the asymmetric carbon atom in formula I

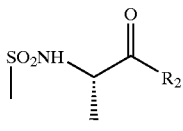

had the S configuration.

7. A compound according to claim 2 wherein the asymmetric carbon atom in formula I

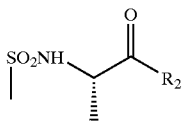

had the S configuration.

8. A compound according to claim 3 wherein the asymmetric carbon atom in formula I

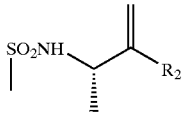

had the S configuration.

9. A compound according to claim 4 wherein the asymmetric carbon atom in formula I

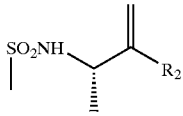

had the S configuration.

10. A process for preparing a compound according to claim 1 in which X is $CR_4$— which comprises reacting a compound of formula (V)

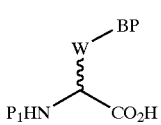
(V)

in which $P_1$ is a protecting group and P is a protecting group or hydrogen with a compound of formula (VI)

$R_2H$  (VI)

to give a compound of formula (IV)

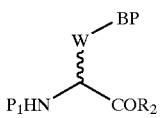
(IV)

which is then treated with hydrogen chloride to give a compound of formula (III) as a hydrochloride salt

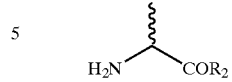
(III)

which, in turn is condensed with a compound of formula (II)

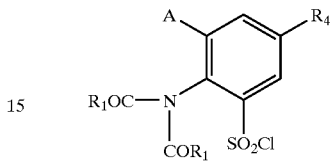
(II)

followed by a hydrogenolysis when it is desired to obtain a compound of formula (I) in which $R_4$ is hydrogen, A, B, W, $R_1$, $R_2$ and $R_4$ in the above formulas having the meanings given in claim 1.

11. A process for preparing a compound according to claim 1 in which X is $CR_4$— which comprises reacting a compound of formula (III) in which P represents a hydrogen atom

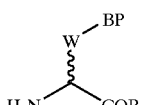
(III)

with a compound of formula (IIa)

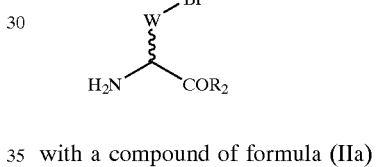
(IIa)

to give a compound of formula (Ia)

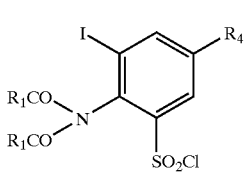
(Ia)

which is then coupled with a compound of formula (VII)

$A—Sn(R_5)_3$  (VII)

in which $R_5$ is a $(C_1-C_4)$alkyl group, followed by a hydrogenolysis when it is desired to obtain the compound of formula (I) in which $R_4$ is hydrogen, A, B, W, $R_1$, $R_2$ and $R_4$ in the above formulas having the meanings given in claim 1.

12. A process for preparing a compound according to claim 1 in which X is a nitrogen atom which comprises coupling a compound of formula (III)

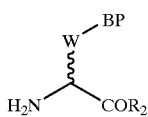

with a compound of formula (XV)

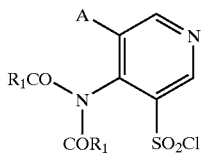

A, B, W, $R_1$ and $R_2$ having the meanings given in claim 1.

13. A compound of formula (III)

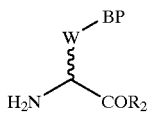

wherein B, W and $R_2$ are as defined in claim 1 and P is a protecting group or hydrogen, or a hydrochloride salt thereof.

14. A compound of formula XV

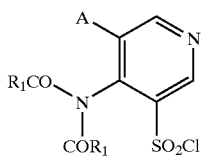

in which A and $R_1$ are as defined in claim 1.

15. A pharmaceutical composition comprising a therapeutically effective amount of a compound according to claim 1 together with a pharmaceutically acceptable excipient.

16. A pharmaceutical composition comprising a therapeutically effective amount of a compound according to claim 2 together with a pharmaceutically acceptable excipient.

17. A pharmaceutical composition comprising a therapeutically effective amount of a compound according to claim 3 together with a pharmaceutically acceptable excipient.

18. A pharmaceutical composition comprising a therapeutically effective amount of a compound according to claim 4 together with a pharmaceutically acceptable excipient.

19. A pharmaceutical composition comprising a therapeutically effective amount of a compound according to claim 5 altogether with a pharmaceutically acceptable excipient.

20. A method for the treatment of thrombosis which comprises administering to a patient in need of such treatment a therapeutically effective amount of a compound according to claim 1.

21. A method for the treatment of thrombosis which comprises administering to a patient in need of such treatment a therapeutically effective amount of a compound according to claim 2.

22. A method for the treatment of thrombosis which comprises administering to a patient in need of such treatment a therapeutically effective amount of a compound according to claim 3.

23. A method for the treatment of thrombosis which comprises administering to a patient in need of such treatment a therapeutically effective amount of a compound according to claim 4.

24. A method for the treatment of thrombosis which comprises administering to a patient in need of such treatment a therapeutically effective amount of a compound according to claim 5.

25. A method for the prevention of thrombus formation in a patient in need thereof which comprises administering to said patient an anticoagulation effective amount of a compound according to claim 1.

26. A method for the prevention of thrombus formation in a patient in need thereof which comprises administering to said patient an anticoagulation effective amount of a compound according to claim 2.

27. A method for the prevention of thrombus formation in a patient in need thereof which comprises administering to said patient an anticoagulation effective amount of a compound according to claim 3.

28. A method for the prevention of thrombus formation in a patient in need thereof which comprises administering to said patient an anticoagulation effective amount of a compound according to claim 4.

29. A method for the prevention of thrombus formation in a patient in need thereof which comprises administering to said patient an anticoagulation effective amount of a compound according to claim 5.

* * * * *